(12) United States Patent
He et al.

(10) Patent No.: US 8,900,149 B2
(45) Date of Patent: Dec. 2, 2014

(54) WALL MOTION ANALYZER

(75) Inventors: Xingbai He, Andover, MA (US); Alice M. Chiang, Weston, MA (US)

(73) Assignee: Teratech Corporation, Burlington, MA (US)

( * ) Notice: Subject to any disclaimer, the term of this patent is extended or adjusted under 35 U.S.C. 154(b) by 678 days.

(21) Appl. No.: 10/817,316

(22) Filed: Apr. 2, 2004

(65) Prior Publication Data

US 2005/0228276 A1    Oct. 13, 2005

(51) Int. Cl.
*A61B 8/00* (2006.01)
*A61B 8/08* (2006.01)
*A61N 1/365* (2006.01)
*A61B 8/14* (2006.01)

(52) U.S. Cl.
CPC ............... *A61B 8/543* (2013.01); *A61B 8/0883* (2013.01); *A61B 8/461* (2013.01); *A61B 8/463* (2013.01); *A61B 8/488* (2013.01); *A61B 8/56* (2013.01); *A61N 1/36528* (2013.01); *A61B 8/14* (2013.01)
USPC ....................................................... 600/453

(58) Field of Classification Search
USPC ........... 600/428, 441, 449, 450, 453; 607/2, 9
See application file for complete search history.

(56) References Cited

U.S. PATENT DOCUMENTS

| | | | |
|---|---|---|---|
| 5,247,938 A | 9/1993 | Silverstein et al. | 128/662.03 |
| 5,515,856 A | 5/1996 | Olstad et al. | 128/661.04 |
| 5,590,658 A | 1/1997 | Chiang et al. | 128/661.01 |
| 5,690,114 A | 11/1997 | Chiang et al. | 128/661.01 |
| 5,701,897 A | 12/1997 | Sano | 128/661.09 |
| 5,800,356 A * | 9/1998 | Criton et al. | 600/441 |
| 5,839,442 A | 11/1998 | Chiang et al. | 128/661.01 |
| 5,846,200 A | 12/1998 | Schwartz | 600/443 |
| 5,882,315 A | 3/1999 | Ji et al. | 600/553 |
| 5,904,652 A | 5/1999 | Gilbert et al. | 600/447 |
| 5,957,846 A | 9/1999 | Chiang et al. | 600/447 |
| 5,961,462 A | 10/1999 | Loupas et al. | 600/453 |
| 5,964,709 A | 10/1999 | Chiang et al. | 600/447 |
| 6,102,859 A | 8/2000 | Mo | 600/443 |
| 6,106,472 A | 8/2000 | Chiang et al. | 600/447 |
| 6,111,816 A | 8/2000 | Chiang et al. | 367/7 |
| 6,139,501 A | 10/2000 | Roundhill et al. | 600/443 |
| 6,186,950 B1 | 2/2001 | Averkiou et al. | 600/443 |
| RE37,088 E | 3/2001 | Olstad et al. | 600/440 |
| 6,248,073 B1 | 6/2001 | Gilbert et al. | 600/447 |

(Continued)

OTHER PUBLICATIONS

St. John Sutton, Martin G. MD, et al., "Effect of Cardiac Resynchronization Therapy on Left Ventricular Size and Function in Chronic Heart Failure," *Circulation*, pp. 1985-1990 (Apr. 22, 2003).

(Continued)

*Primary Examiner* — Jonathan Cwern
(74) *Attorney, Agent, or Firm* — McCarter & English, LLP

(57) ABSTRACT

A system and method for real-time quantitative analysis of heart wall motion is provided. A Doppler imaging system is used to monitor the movement of a heart, or other organ. A B-mode reference image of the target organ is made and then a region-of-interest is defined through the use of a gate. Then pulsed wave spectral tissue Doppler data of the region-of-interest is formed and used to determine the velocity of a region of the target organ. The system may be used for determining appropriate biventricular pacemaker settings for patients suffering from heart disease.

26 Claims, 23 Drawing Sheets

(56) References Cited

U.S. PATENT DOCUMENTS

| | | |
|---|---|---|
| 6,292,433 B1 | 9/2001 | Gilbert et al. ............... 367/138 |
| 6,306,089 B1 | 10/2001 | Coleman et al. ............ 600/437 |
| 6,379,304 B1 | 4/2002 | Gilbert et al. ............... 600/447 |
| 6,447,453 B1 | 9/2002 | Roundhill et al. ........... 600/443 |
| 6,447,454 B1 | 9/2002 | Chenal et al. ............... 600/449 |
| 6,450,959 B1 * | 9/2002 | Mo et al. ..................... 600/441 |
| 6,491,636 B2 | 12/2002 | Chenal et al. ............... 600/450 |
| 6,512,481 B1 | 1/2003 | Velazquez et al. ........... 342/367 |
| 6,517,485 B2 | 2/2003 | Torp et al. ................... 600/438 |
| 6,530,887 B1 | 3/2003 | Gilbert et al. ............... 600/459 |
| 6,537,221 B2 | 3/2003 | Criton et al. ................ 600/454 |
| 6,552,964 B2 | 4/2003 | Chiang et al. ............... 367/138 |
| 6,593,880 B2 | 7/2003 | Velazquez et al. ........... 342/367 |
| 6,638,221 B2 | 10/2003 | Abe et al. .................... 600/437 |
| 6,638,226 B2 | 10/2003 | He et al. ...................... 600/443 |
| 6,669,633 B2 | 12/2003 | Brodsky et al. .............. 600/437 |
| 6,671,227 B2 | 12/2003 | Gilbert et al. ............... 367/138 |
| 6,676,599 B2 | 1/2004 | Torp et al. ................... 600/437 |
| 6,721,235 B2 | 4/2004 | Chiang et al. ............... 367/138 |
| 7,022,078 B2 * | 4/2006 | Heimdal et al. ............. 600/453 |
| 7,041,061 B2 | 5/2006 | Kramer et al. |
| 7,211,045 B2 * | 5/2007 | Dala-Krishna et al. ....... 600/441 |
| 2003/0216646 A1 | 11/2003 | Angelsen et al. |
| 2003/0225330 A1 | 12/2003 | Wong |
| 2005/0043895 A1 * | 2/2005 | Schechter .................... 702/19 |
| 2011/0190631 A1 | 8/2011 | Kramer et al. |

OTHER PUBLICATIONS

Breithardt, Ole A. MD, et al., "Echocardiographic Quantification of Left Ventricular Asynchrony Predicts an Acute Hemodynamic Benefit of Cardiac Resynchronization Therapy," *Journal of the American College of Cardiology*, vol. 40, No. 3: 536-545 (2002).

Pitzalis, Maria Vittoria, MD, PhD., et al., "Cardiac Resynchronization Therapy Tailored by Echocardiographic Evaluation of Ventricular Asynchrony," *Journal of the American College of Cardiology*, vol. 40, No. 9.: 1615-1622 (2002).

Søgaard, Peter MD, DMSc, et al., "Tissue Doppler Imaging Predicts Improved Systolic Performance and Reversed Left Ventricular Remodeling During Long-Term Cardiac Resynchronization Therapy," *Journal of the American College of Cardiology*, vol. 40, No. 4: 723-730 (2002).

• Verrnon, PA-Cath Information, Jan. 2001.

Sogaard et al., "Tissue doppler imaging predicts improved systolic performance and reversed left ventricular remodeling during long-term cardiac resynchronization therapy," ScienceDirect, Journal of the American College of Cardiology, vol. 40, Issue 4, Aug. 2002, pp. 723-730.

* cited by examiner

Septal (dashed line) and lateral (solid line) wall motion

WALL MOTION ANALYZER

BACKGROUND OF THE INVENTION

Heart disease affects the lives of thousands of persons each year in the United States. And, as the U.S. population ages, the annual number of heart disease-related deaths is expected to grow. A percentage of these deaths can be postponed or eliminated if diagnosed and treated early. Furthermore, early diagnosis and treatment often improves the quality of life for afflicted individuals as well as reduce the overall cost of treatment because usage of acute care facilities, such as operating rooms, intensive care units, and rehabilitation facilities, is reduced or eliminated.

One common heart abnormality is caused by insufficient blood supply to portions of the heart muscle (myocardium). This abnormality may be referred to as focal wall abnormality (WMA), and is characterized by dysynchronous contraction of the left ventricle of the heart. WMAs decrease the overall performance of the left ventricle and correspondingly increase the workload on the heart, which may lead to premature heart failure.

If properly diagnosed, patients suffering from WMA may be treated using cardiac resynchronization therapy (CRT) for restoring synchronous contraction of the interventricular septum and the left ventricular free wall. CRT is achieved through the use of a pacemaker capable of biventricular pacing. However, before CRT can be undertaken, a proper diagnosis must be made which includes detection of WMA and determination of the proper settings for encoding into the pacemaker. Quantitative measurements are desired for efficient and accurate diagnosis of WMA. Accurate identification of the ventricular borders is useful for determining the volume of the left ventricle and for determining the ejection fraction (EF) which refers to the portion of blood that is pumped out of the filled ventricle as a result of a heart beat. Accurate identification of ventricular borders also makes possible generation of time-volume curves so a diagnostician does not have to rely on estimates of left ventricular volumes.

Identification of ventricular borders is problematic using prior art techniques because they require highly trained diagnosticians for reliable interpretation of heart data. In addition, prior art techniques do not produce quantitative analyses for detection, tracing and display of heart data.

What is needed is a method and apparatus for making on-line quantitative analyses of moving tissue and in particular of heart data, such as cardiac function and ventricular wall motion for facilitating the detection, tracking and display of information about cardiac size, morphology and function for routine clinical use.

SUMMARY OF THE INVENTION

In accordance with an aspect of the invention, a method for quantitatively measuring tissue movement is provided. An ultrasound imaging system is provided and a B-mode reference image of moving tissue is formed. A gate defining a region-of-interest of the tissue is formed. Then, pulsed wave spectral tissue Doppler data of the region-of-interest is formed and a displacement of the tissue within the region-of-interest is determined. The method may further include forming a tissue Doppler image of the tissue and forming the gate using the tissue Doppler image. In another aspect of the invention, forming the gate may include, among other things, forming first and second pulsed wave spectral Doppler lines to define the region-of-interest.

The systems and methods of preferred embodiments of the invention can use external or internal probes with a transducer configuration adapted for a particular application. A preferred embodiment of the invention relates to the use of external probes for imaging and quantification of heart wall motion. Echocardiography is used to measure displacement of the septal and left ventricular free wall to provide for the evaluation of cardiac function and the diagnosis of ventricular wall motion dysynchrony. In another preferred embodiment of the invention internal probes such as ultrasound catheters or endoscopic transducers can be used to quantitatively measure the movement of body lumens or cavities such as the gastrointestinal tract. The wall being evaluated can be any wall in the digestive tract such as the wall of the esophagus, the stomach, the large intestine, the colon, the rectum or other organs including the bladder.

In accordance with another aspect of the invention, a method for providing operating parameters for a biventricular pacemaker includes performing an echocardiographic imaging process to provide quantitative data representative of heart wall motion; and selecting lead delay settings for a biventricular pacemaker using the quantitative data. The method may further include forming a plurality of gates for the measurement of the lateral wall and septal wall of a heart when performing a Doppler imaging process. In addition, pulsed wave spectral tissue Doppler data of the lateral wall and septal wall may be formed while practicing the method.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1A:
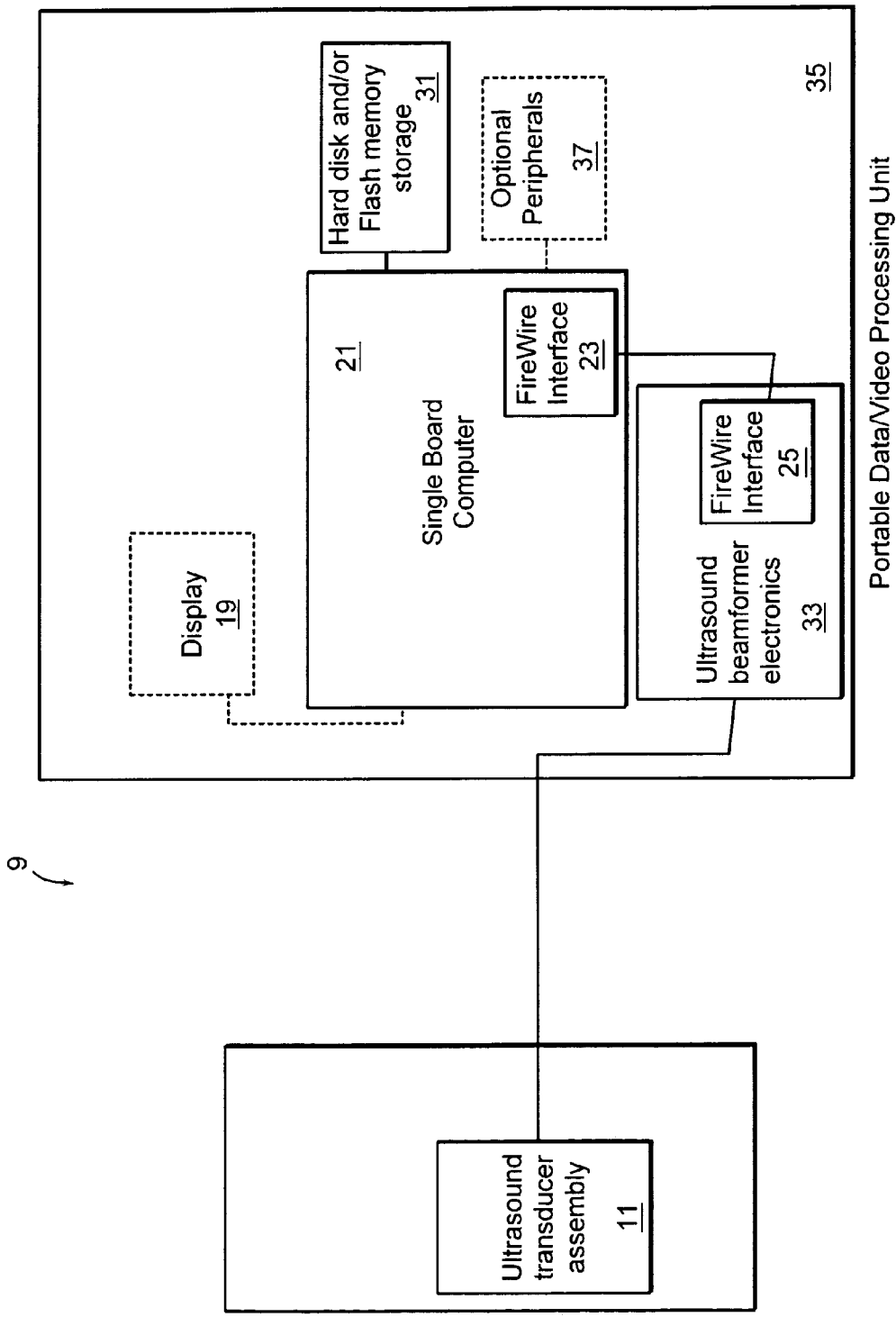
FIGS. 1A-1C illustrate embodiments of the invention capable of performing real-time analysis of heart wall motion.

With reference to the figures, a detailed discussion of certain embodiments of the present invention is presented. Notably, the present invention may be implemented using software, hardware or any combination thereof, as would be apparent to those of skill in the art.

Therefore, unless otherwise specified, illustrated embodiments can be understood as providing exemplary features of varying detail of certain embodiments, and therefore, unless otherwise specified, features, components modules, and/or aspects of the illustrations can be otherwise combined, separated, interchanged and/or rearranged without departing from the disclosed systems and methods. Additionally, the shapes and sizes of components are also exemplary and unless otherwise specified, can be altered without affecting the disclosed systems or methods. Accordingly, illustrative figures and/or examples used hereinbelow are not meant to limit the scope of the present invention or its embodiments or equivalents.

Echocardiography encompasses all aspects of the development and use of products and systems that capture, display, store, integrate, measure and report on ultrasound-derived cardiovascular images for diagnostic and therapeutic medical purposes. Historically, extensive, off-line post-imaging processing techniques have been developed for qualitative and quantitative analyses of cardiac size, morphology and function. Embodiments of the invention include a wall motion analyzer that provides all echocardiographic imaging modes (including B-mode, pulse-wave Doppler, color flow, etc.) and performs real-time, on-line quantitative image and data analysis for facilitating detecting, tracking and displaying information about cardiac size, morphology and function in a manner suitable for routine clinical use. Such information improves the accuracy and functionality of echocardiography for detection and monitoring of cardiovascular disease.

The invention can also provide strain images and strain-rate analysis through the analysis of multi-gate Pulsed Wave Spectral Tissue Doppler data. Furthermore, an accurate method for real-time evaluation of cardiac function and identification of ventricular wall motion dysynchrony using quantitative analysis of B-mode images is provided. And, an automatic border detection (ABD) technique is presented for delineating and tracking the movement of left ventricular endocardial contours as well as to aid with more accurate determination of left ventricular volumes and ejection fraction (EF). Use of ABD in accordance with aspects of the invention also facilitates generation of time-volume curves, and not merely estimates of left ventricular volumes at only two time points, thus saving time and cost, while allowing routine quantitative measures of left ventricular chamber size and EF to be performed in real time. Furthermore, ABD may be more accurate than novice readers, providing more reliable estimates of cardiac function than was possible using prior art processes. Finally, ABD can help in regional function assessment by allowing quantitative measurement of relative delays in contraction.

BiVentricular (BiV) Cardiac Resynchronization Therapy (CRT) is a promising therapeutic option for patients with severe heart failure and dysynchronous ventricular contraction. Currently, setting of optimal delays between right and left ventricular leads is determined by looking at the electrocardiogram (ECG). A wide QRS complex is indicative of ventricular dysynchrony, so delays are adjusted until a narrow QRS is observed. However, there exists a significant fraction of patients who derive little or no benefit from BiV pacing despite achieving a narrow QRS on the ECG. An embodiment of the invention allows direct imaging of the left ventricle walls and their relative motion during lead-delay setting, thus alleviating the need to monitor the width of the ECG, since it may not reflect actual regional wall motion. Echocardiography is the imaging modality of choice for this task as it has high spatial and temporal resolution, is portable and is suitable for use in the electrophysiology laboratory.

Echo techniques, such as Tissue Doppler imaging (TDI) and three-dimensional echo, enable accurate quantification of regional and global left ventricle function and volumes. From digitally recorded TDI loops of one or more heart beats, two TDI modalities have been derived, namely tissue tracking (TT) and strain rate (SR) analysis. Both TT and SR may be useful for the evaluation of regional myocardial pathophysiology before and after intervention to assess the effect of CRT. Furthermore, echo phase analysis of endocardial wall motion in the radial direction demonstrates that optimized CRT improves left ventricle performance by synchronizing septal and free wall contraction. Direct echocardiographic visualization may also help to distinguish between patients who would and would not benefit from CRT.

Figure 1B:
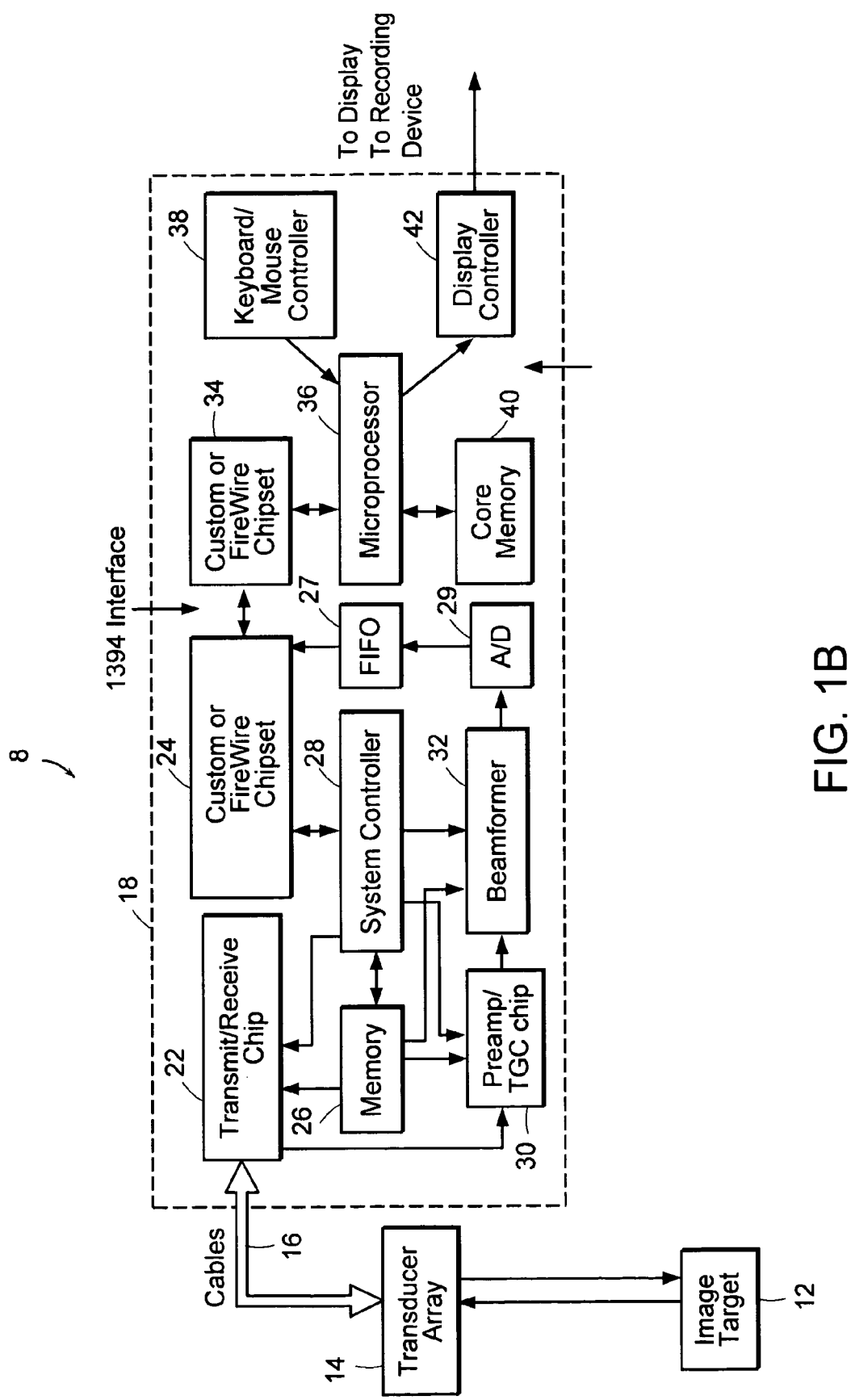
Figure 1C:
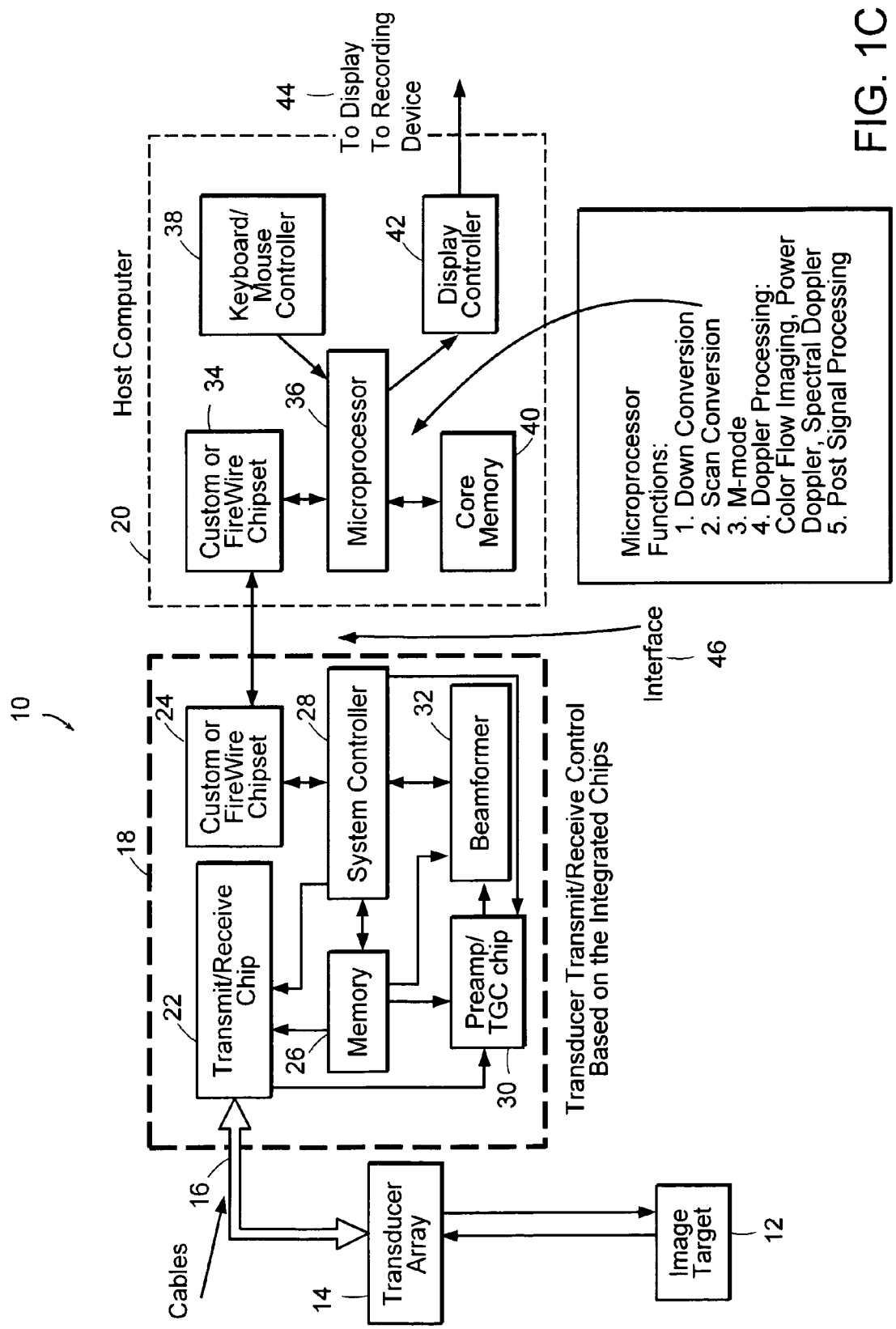

FIGS. 1A-C illustrate various schematic embodiments of the invention.

FIG. 1A illustrates an exemplary ultrasound imaging system 9 comprising an ultrasound transducer assembly 11, and a portable data/video processing unit 35. Transducer assembly 11 transmits ultrasonic signals into a region-of-interest, or target area, here the human heart. In addition, transducer assembly 11 receives ultrasonic signals reflected from the region of interest and conditions them before conveying them to processing unit 35.

Processing unit 35 comprises ultrasound beamformer electronics 33, FireWire interfaces 23, 25, single board computer 21, hard disk/flash memory storage 31, a display 19 and optional peripherals 37. The output of transducer assembly 11 is received by beamformer electronics 33. Beamformer electronics 33 receives the conditioned signals and introduces appropriate differential delays into each of the received signals to dynamically focus the signals such that an accurate image can be created. These dynamically focused signals are referred to as beamformed signals. Further details of exemplary beamforming electronics 33 and delay circuits used to introduce differential delay into received signals and the pulses generated by a pulse synchronizer are described in U.S. Pat. No. 6,111,816 to Alice M. Chiang et al., issued Aug. 29, 2000 entitled "Multi-Dimensional Beamforming Device," the entire content of which is incorporated herein by reference. Beamformed signals are then conveyed from FireWire interface 25 to FireWire interface 23. "FireWire" refers to IEEE standard 1394, which provides high-speed data transmission over a serial link. There also exists a wireless version of the FireWire standard allowing communication via an optical link for untethered operation.

The FireWire standard and an ultrasound probe with integrated electronics as described in U.S. Pat. No. 6,783,493, issued on Aug. 31, 2004, entitled "Ultrasound Probe With Integrated Electronics," by Alice M. Chiang et al., the entire contents of which are incorporated herein by reference, may be used in preferred embodiments of the present invention. The FireWire standard is used for multimedia equipment and allows 100-200 Mbps and preferably in the range of 400-800 Mbps operation over an inexpensive 6 wire cable. Power is also provided on two of the six wires so that the FireWire cable is the only necessary electrical connection to the probe head. A power source such as a battery or IEEE 1394 hub can be used. The FireWire protocol provides both isochronous communication for transferring high-rate, low-latency video data as well as asynchronous, reliable communication that can be used for configuration and control of the peripherals as well as obtaining status information from them. Several chipsets are available to interface custom systems to the FireWire bus. Additionally, PCI-to-FireWire chipsets and boards are currently available to complete the other end of the head-to-host connection. CardBus-to-FireWire boards can also be used.

FireWire interface 23 provides the beamformed signals to single board computer 21. Single board computer 21 may comprise, among other things, a processor, main memory, read only memory (ROM), storage device (collectively hard disk and/or flash storage 31), bus, display 19, keyboard, cursor control, and communication interface (collectively optional peripherals 37).

The processor may be any type of conventional processing device that interprets and executes instructions. The main memory may be a random access memory (RAM) or a similar dynamic storage device for storing information and instructions to be executed by the processor. In addition, the main memory may also be used for storing temporary variables or other intermediate information during execution of instructions by the processor. A ROM may store static information and instructions for use by the processor. It will be appreciated that the ROM may be replaced with some other type of static storage device such as a flash memory card. The data storage device may include any type of magnetic or optical media and its corresponding interfaces and operational hardware. The data storage device stores information and instructions for use by the processor. The bus includes a set of hardware lines (conductors, optical fibers, or the like) that allow for data transfer among the components of single board computer 21.

The display device 19 may be a cathode ray tube (CRT), or the like, for displaying information to a user. The keyboard and cursor control allow the user to interact with the single board computer 21. The cursor control may be, for example, a mouse. In an alternative configuration, the keyboard and cursor control can be replaced with a microphone and voice recognition means to enable the user to interact with the single board computer 21.

The communication interface enables the single board computer 21 to communicate with other devices/systems via any communications medium. For example, communication interface may be a modem, an Ethernet interface to a LAN, or a printer interface. Alternatively, the communication interface can be any other interface that enables communication between the single board computer 21 and other devices or systems.

FIG. 1B illustrates a second exemplary embodiment of an ultrasound imaging system 8. System 8 comprises a transducer array 14 operating in essentially a similar manner as ultrasound transducer assembly 11. In addition, system 8 comprises a transmit/receive chip 22, Custom or FireWire Chipset 24, a memory 26, a system first-in-first-out (FIFO) register 27, a system controller 28, an analog-to-digital converter (A/D) 29, a preamp/TGC chip 30 and, a beamformer 32.

System 8 may further comprise a second custom or FireWire Chipset 34, a microprocessor 36, a keyboard/mouse controller 38, a core or main memory 40 and a display controller 42, a front-end interface or processing unit 18 which is connected by cables 16, for example, coaxial cables to the transducer array 14 and includes a transducer transmit/receive control chip 22. Alternatively, front-end interface unit 18 may be communicatively coupled to transducer array 14 via free space radio frequency (RF) or optical means.

Ultrasonic echoes reflected by the image target 12 are detected by the ultrasonic transducers in the array 14. Each transducer converts the received ultrasonic signal into a representative electrical signal which may be forwarded to an integrated chip having preamplification circuits and time-varying gain control (TGC) circuitry 30. The preamplification circuitry can set the level of the electrical signals from the transducer array 14 to a level suitable for subsequent processing, and the TGC circuitry can be used to compensate for attenuation of the sound pulse as it penetrates through human tissue. In addition, the TGC circuit may also drive beamforming circuits 32 to produce a line image.

A memory 26 stores data from system controller 28. Memory 30 provides stored data to the transmit/receive chip 22, the TGC 30 and the beamformer 32. The output from the system controller 28 may be connected directly to an output interface such as a custom or FireWire Chipset. An exemplary FireWire Chipset for use in ultrasonic imaging applications is described in co-pending U.S. patent application Ser. No.

09/449,780, entitled "Ultrasound Probe with Integrated Electronics," by Jeffrey M. Gilbert et al., the entire contents of which are being incorporated herein by reference.

FIG. 1C is a schematic functional block diagram of an exemplary embodiment of an ultrasound imaging system 10 that can be used for practicing aspects of the invention. Similar imaging systems are described in U.S. Pat. No. 5,957,846 to Alice M. Chiang et al., issued Sep. 28, 1999, entitled "Portable Ultrasound Imaging System," the entire contents of which are being incorporated herein by reference. Ultrasonic imaging system 10 may comprise a transducer array 14, cables 16, a transducer transmit/receive control module 18 compressing a transmit/receive chip 22, a customer Firewire chip set 24, 34, a memory 26, a system controller 28, a preamp/TGC Chip 30, and a beamforming module 32. System 10 also comprises a host computer further compressing a microprocessor 36, a keyboard/mouse controller 38, a core memory 40 and a display controller 42. An interface array 46 may be employed for communicatively coupling transducer transmit/receive control module 18 to host computer 20. Host computer 20 may take the form of a laptop computer, a desk top computer, a workstation, a personal digital assistant or any other form factor comprising the functionality of components of host computer 20 shown in FIG. 1C.

The microprocessor 36 also controls the memory 40 which stores data in a machine-readable format. It is understood that the memory 40 can be a single memory or can be multiple memory circuits. The microprocessor 36 also interfaces with the post signal processing functional instructions and the display controller 42 to control their individual functions. The display controller 42 may compress data to permit transmission of the image data to remote stations for display and analysis via a transmission channel. The transmission channel can be a modem or wireless cellular communication channel or other known communication method.

Transmit/receive chip 22 may include a VRAM/SDRAM controller for directly controlling the ultrasound scan head, while higher level control, initialization, and data processing and display may come from a general purpose host such as a desktop PC, laptop, or palmtop computer. The host computer 20 writes the VRAM/DRAM data via a VRAM/SDRAM Controller. This is performed both at initialization as well as whenever any parameters change (such as number or positions of zones, or types of scan head) requiring a different scanning pattern. During routine operation when data is being continually read from the scan head with the same scanning parameters, the host computer 20 need not write to the VRAM/SDRAM. Because the VRAM/SDRAM controller also tracks where in the scan pattern it is, it can perform the packetization to mark frame boundaries in the data that goes back to the host. The control of additional functions such as power-down modes and querying of buttons or other controls on the transducer probe head can also be performed via the FireWire connection.

Although FireWire chipsets 24, 34 manage electrical and low-level protocol interface to the FireWire interface, the system controller 28 manages the interface to the FireWire chipset 24 as well as handling higher level FireWire protocol issues such as decoding asynchronous packets and keeping frames from spanning isochronous packet boundaries.

Asynchronous data transfer occurs at anytime and is asynchronous with respect to image data. Asynchronous data transfers may take the form of a write or read request from one node to another. The writes and the reads are to a specific range of locations in the target node's address space. The address space can be any size; however, in a preferred embodiment a 48 bit address space is used. The individual asynchronous packet lengths may be limited to 1024 bytes for 200 Mbps operation. Both reads and writes are supported by the system controller. Asynchronous writes are used to allow the host to modify the VRAM/SDRAM data as well as a control word in the controller which can alter the operation mode. Asynchronous reads are used to query a configuration ROM (in the system controller field programmable gate array [FPGA]) and can also be used to query external registers or I/O such as a "pause" button. The configuration ROMs contain a queryable "unique ID" which can be used to differentiate the probe heads as well as allow node-lockings of certain software features based on a key.

Using isochronous transfers, a node may reserve a specified amount of bandwidth to receive guaranteed low-overhead bursts of link access at certain intervals, say for example, every 1/8000 second. All image data from the head to the host is sent via isochronous packets. The FireWire protocol allows for some packet-level synchronization and additional synchronization is built into the system controller.

The-front-end processing or interface unit system controller 28 interfaces with a host computer 20, such as a desktop PC, laptop or palmtop, via the custom or FireWire chipsets 24, 34. This interface allows the host to write control data to and to receive data from the memory 26. This may be performed at initialization and whenever a change in parameters such as, for example, number and/or position of zones, is required when the user selects a different scanning pattern. The front-end system controller 28 also provides buffering and flow control functions, as data from the beamformer is sent to the host via a bandwidth-constrained link, to prevent data loss.

Host computer 20 may further include a processing unit such as microprocessor 36. In a preferred embodiment of the ultrasound imaging system in accordance with the present invention the microprocessor 36 includes on-chip parallel processing elements. In a preferred embodiment, the parallel processing elements may include a multiplier and an adder. In another preferred embodiment, the processing elements may include computing components, memories, logic and control circuits. Depending on the complexity of the design, the parallel processing elements can execute either Single Instruction Multiple Data (SIMD) or Multiple Instruction Multiple Data (MIMD) instructions.

Further, the host computer 20 includes a memory unit 40 that is connected to the microprocessor 36 and has a sequence of instructions stored therein to cause the microprocessor 36 to provide the functions of down conversion, scan conversion, M-mode, B-mode and Doppler processing which includes Time Doppler Imaging (TDI), power Doppler and spectral Doppler, and any post-signal processing. The down conversion or mixing of sampled analog data may be accomplished by first multiplying sampled data by a complex value and then filtering the data to reject images that have been mixed to nearby frequencies. The outputs of this down-conversion processing are available for subsequent display or Doppler processing.

The scan conversion function may convert the digitized signal data from beamforming circuitry 32 from polar coordinates $(r,\theta)$ to rectangular coordinates $(x,y)$. After the conversion, the rectangular coordinate data can be forwarded for optional post signal processing where it is formatted for display on the display 44 or for compression in a video compression circuit.

The Doppler processing (CFI, PD, spectral Doppler) is used to image target tissue 12 such as the chambers of the heart or flowing blood. In a preferred embodiment, with pulsed Doppler processing, a color flow map is generated. In a preferred embodiment, the CFI, PD, Spectral Doppler computation can be carried out in software running on the host processor 36. Parallel computation units such as those in the Intel® Pentium® and Pentium® III's MMX™ and SSE™ coprocessors allow rapid computation of the required functions. For parallel processing computation, a plurality of microprocessors are linked together and are able to work on different parts of a computation simultaneously. In another preferred embodiment, digital signal processor (DSP) can also be used to perform the task. Such arrangement permits flexibility in changing digital signal processing algorithms and transmitting signals to achieve the best performance as region of interest is changed.

The control circuit, preferably in the form of a microprocessor 36 inside of a personal computer (e.g., desktop, laptop, palmtop), controls the high-level operation of the ultrasound imaging system 10. The microprocessor 36 or a DSP initializes delay and scan conversion memory. The control circuit 36 controls the differential delays introduced in the beamforming circuitry 32 via the memory 26.

Figure 2:
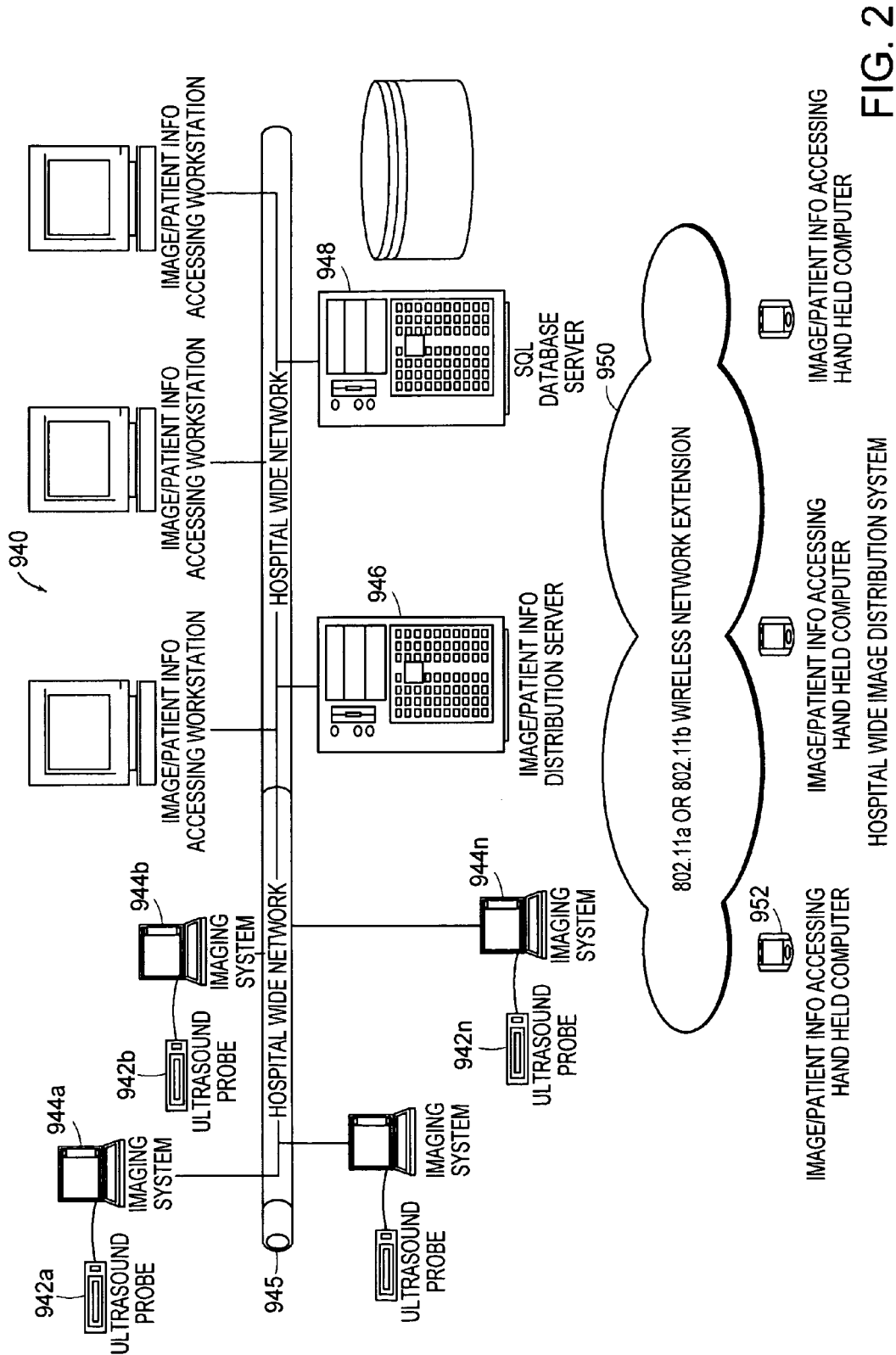
FIG. 2 illustrates an embodiment of the invention employing a data network.

FIG. 2 illustrates an exemplary networked ultrasound image collection and distribution system useful when practicing embodiments of the invention. The main hardware element of the system is ultrasound probe 942a ... n (generally 942). Probe 942 in communication with the laptop computer 944a ... n allows generation of the ultrasound images and related patient information. Laptop computer 944 submits images and information to an image/patient information distribution server 946. The distribution server may utilize an SQL database server 948 for storing and retrieving images and related patient information. The SQL server provides distributed database management. Multiple workstations can manipulate data stored on the server, and the server coordinates operations and performs resource-intensive calculations.

Image viewing software or executable instructions may be implemented in two different embodiments. In a first embodiment, a full stationary version of the image-viewing software instructions may reside on a workstation or laptop computer equipped with high bandwidth connection to hospital network 945. In a second embodiment, a light weight version of the image viewer, or scaled down, image viewing software instructions, may reside on a small PocketPC™ handheld 952 equipped with an IEEE 802.1b and/or IEEE 802.11a compliant network card. A PocketPC image viewer running on handheld 952 may implement only limited functionality allowing basic image viewing operations. Wireless network protocols 950 such as IEEE 802.11 may be used to transmit information to a handheld or other computing devices 952 in communication with a hospital network.

An embodiment as described in FIG. 2 provides an ultrasound imaging system capable of supporting hospital wide image collecting and retrieving needs. System 940 also provides instant access to non-image patient related information. In order to provide inter-hospital information exchange, image distribution servers have the ability to maintain connectivity with each other across wide area networks.

In another preferred embodiment, the probe may directly communicate with a remote computing device such as a PDA 964 using a wireless communication link 950.

Figure 3:
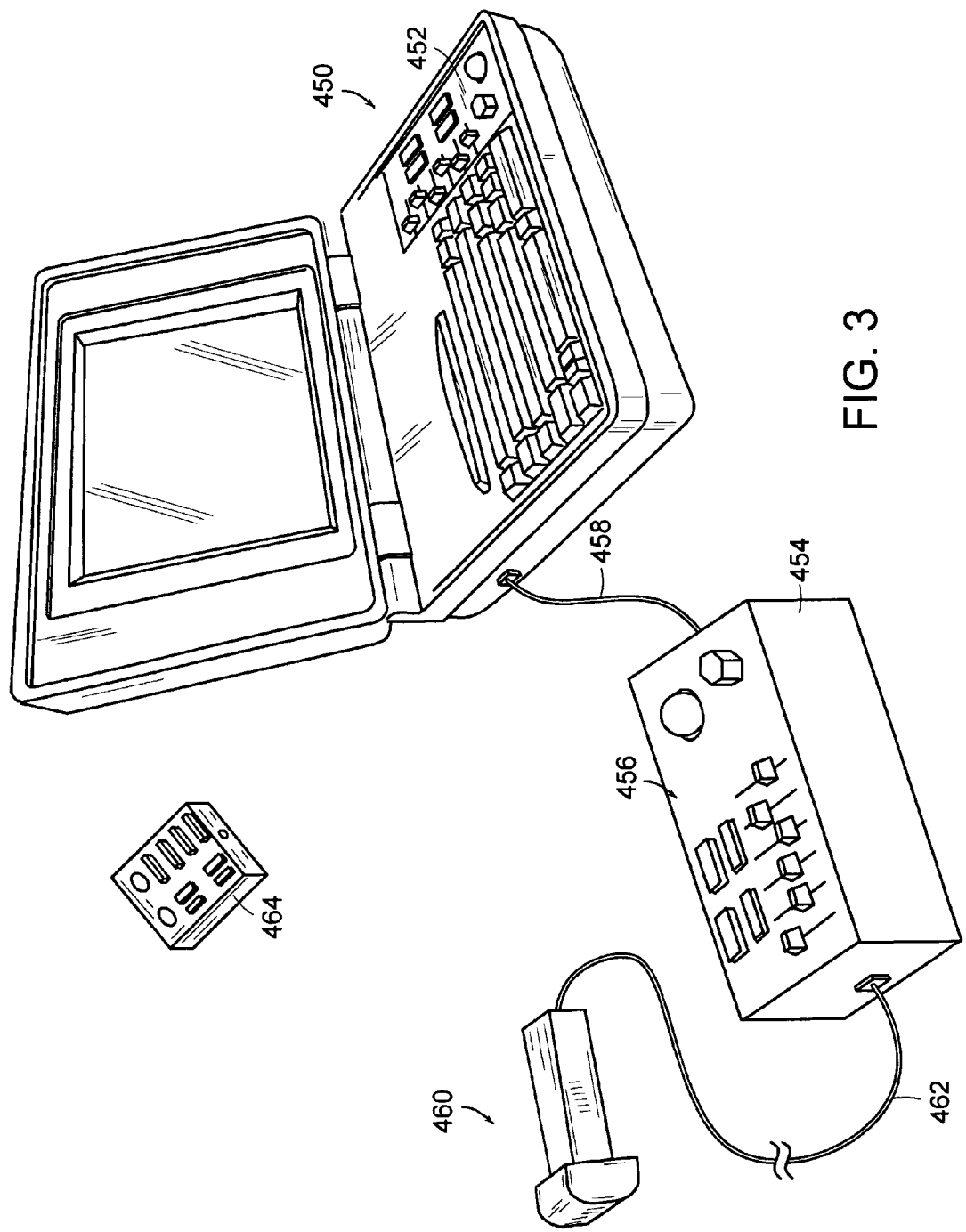
FIG. 3 illustrates a portable embodiment of the invention having a light weight computing and display means associated therewith.

Still another embodiment of the invention is illustrated in FIG. 3 in which a laptop computer 450, having a flat panel display and a standard keyboard, has been programmed to perform scan conversion, Doppler processing, automatic border detection, etc. on a beamformed representation of the region of a heart that has been transmitted from interface housing 454 along a standard communications link such as cable 458 that conforms to the IEEE 1394 FireWire standard or the USB 2.0 standard, for example. The computer 450 and/or the interface can optionally include a control panel 452, 456, that can be customized and used to control the analyses being conducted. A preferred embodiment of the interface housing 454 is controlled solely by the personal computer 450 and provides for the use of standard transducer array probes that can be interchangeably attached to the interface housing 454 with a cable. Alternately, an additional remote controller 464 can be used to control system operation. The interface 454 can house the circuit boards on which the beamformer, memory, system controller and digital communication circuits are mounted. The interface 454 is connected to the hand-held probe 460 with a cable 462 that is preferably between two feet and six feet in length, however longer lengths can be used. The transmit/receive and/or the preamplifier/TGC circuits can be in the probe housing 460 or in the interface housing 454. The computer can also be configured for gigabit Ethernet operation and for transmitting video and image data over networks to remote systems at clinics or hospitals. The video data can also be sent to a VCR or standard video recorder or video camera with an IEEE 1394 part for recording on videotape. The VCR or video camera can be controlled using the computer.

Figure 4:
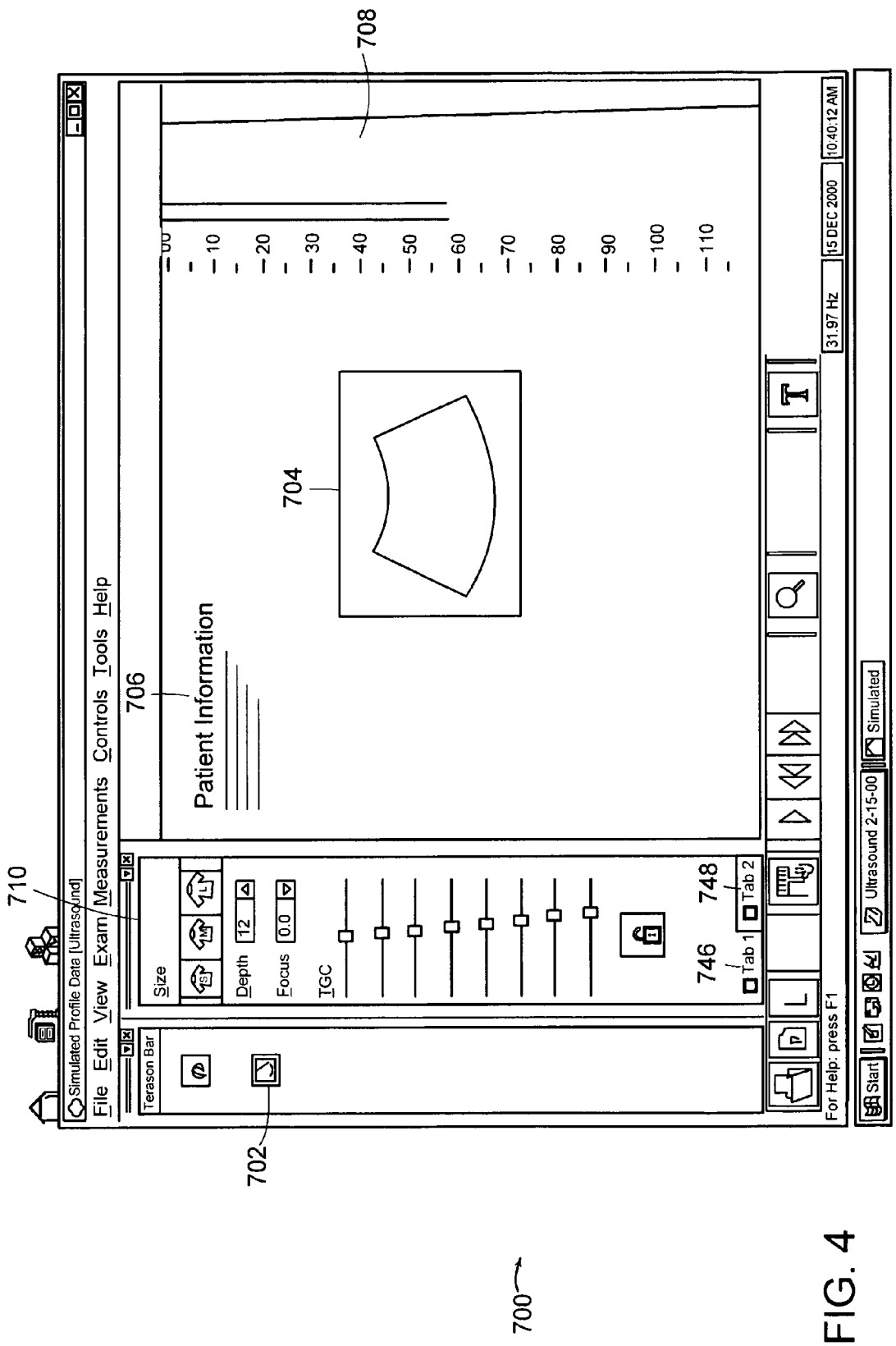
FIG. 4 illustrates an exemplary graphical user interface useful for practicing embodiments of the invention.

FIG. 4 shows an exemplary top-level screen of a graphical user interface 700 (GUI) for controlling and using the ultrasonic imaging system described herein. A selection bar 702 allows the operator to select the active focus areas of the screen. An image area 704 displays the ultrasonic image of the subject area. A patient information area 706 displays information about the subject from whom ultrasonic data is being gathered. A Time Gain Compensation or control (TGC) area 708 provides feedback about time gain compensation, described further below. A control bar 710 allows qualitative and quantitative selection of ultrasonic imaging operations.

These and other embodiments of the invention provide a method for rapid, accurate, quantitative evaluation of cardiac function and ventricular wall motion (dysynchrony) using Duplex or Triplex mode Tissue Doppler Imaging. In addition, strain images and strain rate analyses may be performed using multi-gate Pulsed Wave Spectral Tissue Doppler data. A real time method for evaluation of cardiac function and identification of ventricular wall motion dysynchrony using quantitative analysis of B-mode images is described hereinbelow. The method makes use of an automatic border detection (ABD) technique to delineate and track the movement of left ventricular endocardial contours.

A real-time technique based on duplex (or triplex) Tissue Doppler imaging with simultaneous multiple line-of-sight (direction) pulsed-wave spectral Doppler lines is described hereinbelow. Time integration of Spectral Doppler mean velocities at regions of interest, such as the interventricular septum wall and/or left ventricular free wall, allows computation of displacement data as shown, for example, by equation 1.

$$\vec{d} = \int \vec{v} dt \tag{1}$$

Figure 5:
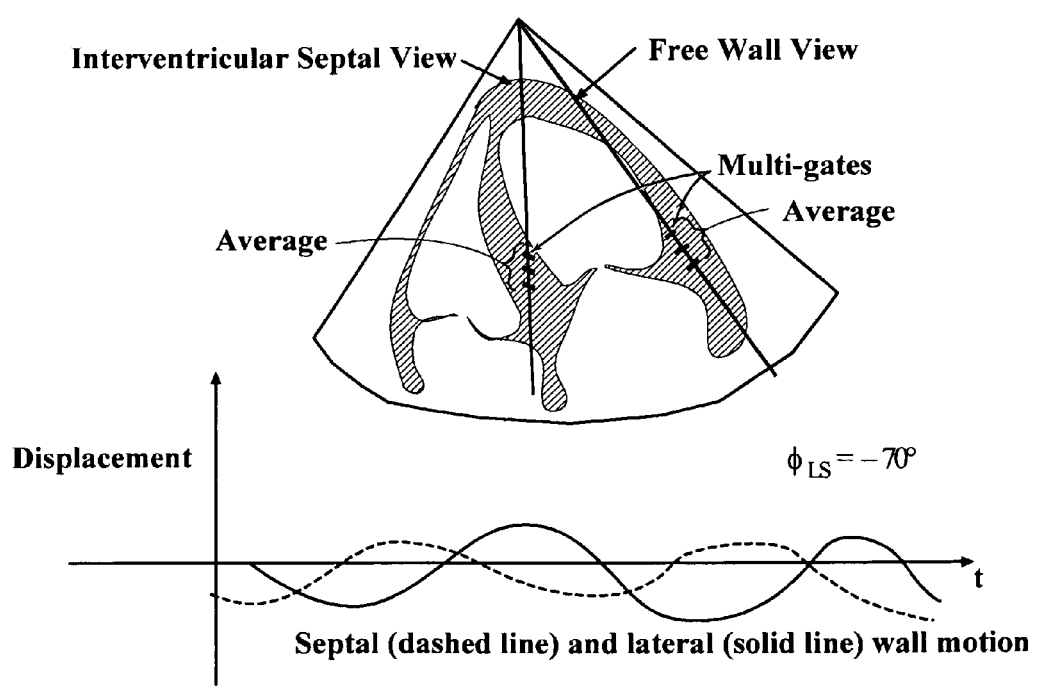
FIG. 5 illustrates an exemplary display showing the quantitative mechanical synchrony between the free wall and septum of the heart.

Use of equation 1 allows for the determination of a time-resolved displacement or contraction, of the interventricular septum and left ventricular free wall over the entire cardiac cycle. The quantitative mechanical synchrony between the free wall and septum may be continuously displayed in a graphical form as shown in FIG. 5 to aid interpretation by a user thereof. In addition, the relative delay between the septum and free wall may be displayed numerically.

By utilizing the invention, multi-directional Pulsed-Wave Spectral Doppler lines may be used. When analyzing the myocardium for tracking wall thickening or thinning in the radial direction, strain rate is used to denote the rate of this relative deformation.

Figure 6:
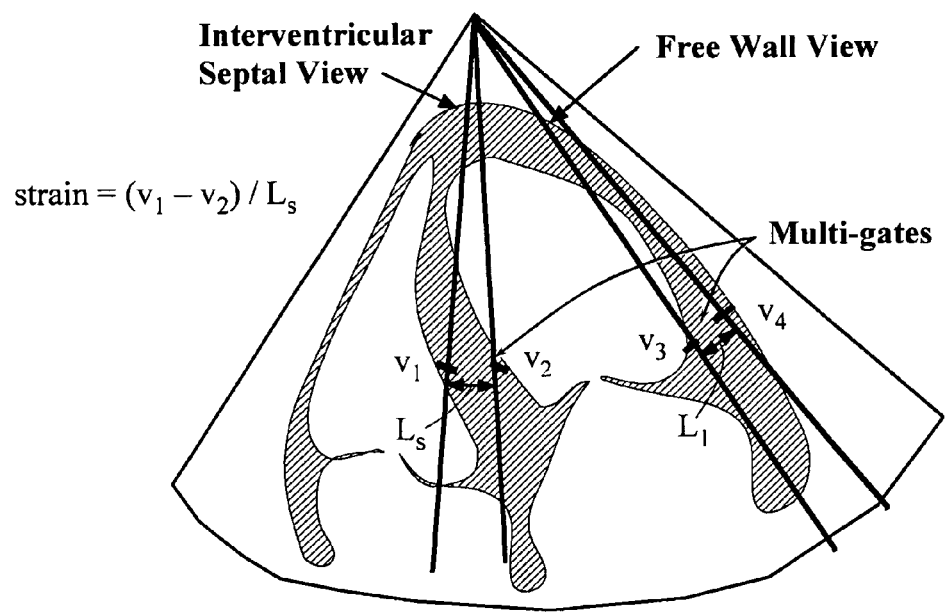
FIG. 6 illustrates an exemplary display for use in determining the strain rate of the septal wall and in particular for performing measurement of strain rate by using multi-direction PW spectral Doppler lines.

FIG. 6 illustrates a display and method for determining the strain rate of the septal wall using equation 2, $$SR = \frac{v_2 - v_1}{L_s} \quad (2)$$

where Ls is the thickness of the septal wall, and the $v_2$ and $v_1$ are mean velocity of the epicardial and endocardial wall respectively.

The interventricular septum and the left ventricular free wall each undergo a cycle of inward and outward movement during a single cardiac cycle in a functioning left ventricle, and each regional movement can be displayed as a displacement curve versus time. A continuous time plot of the displacement curve allows continuous tracking of regional displacement cycles over multiple cardiac cycles. Because of the periodic nature of each displacement curve, the relative movement of these endocardial walls can be analyzed in reference to the phase relationship between curves independent of the displacement magnitude and heart rate. Each regional displacement curve can be modeled as a wave with a period equal to the cardiac cycle interval, which corresponds to the fundamental frequency in Fourier analysis. The time at which the peak of this wave occurs during the cardiac cycle interval is a function of the fundamental frequency phase angle. Using this representation, the magnitude of dysynchrony between two left ventricular walls may be calculated by the difference between their respective phase angles. Phase differences near 0° indicate near-perfect synchrony, whereas a difference of 180 defines maximal dysynchrony, where one wall bulges outward as the other contracts inward.

Figure 7:
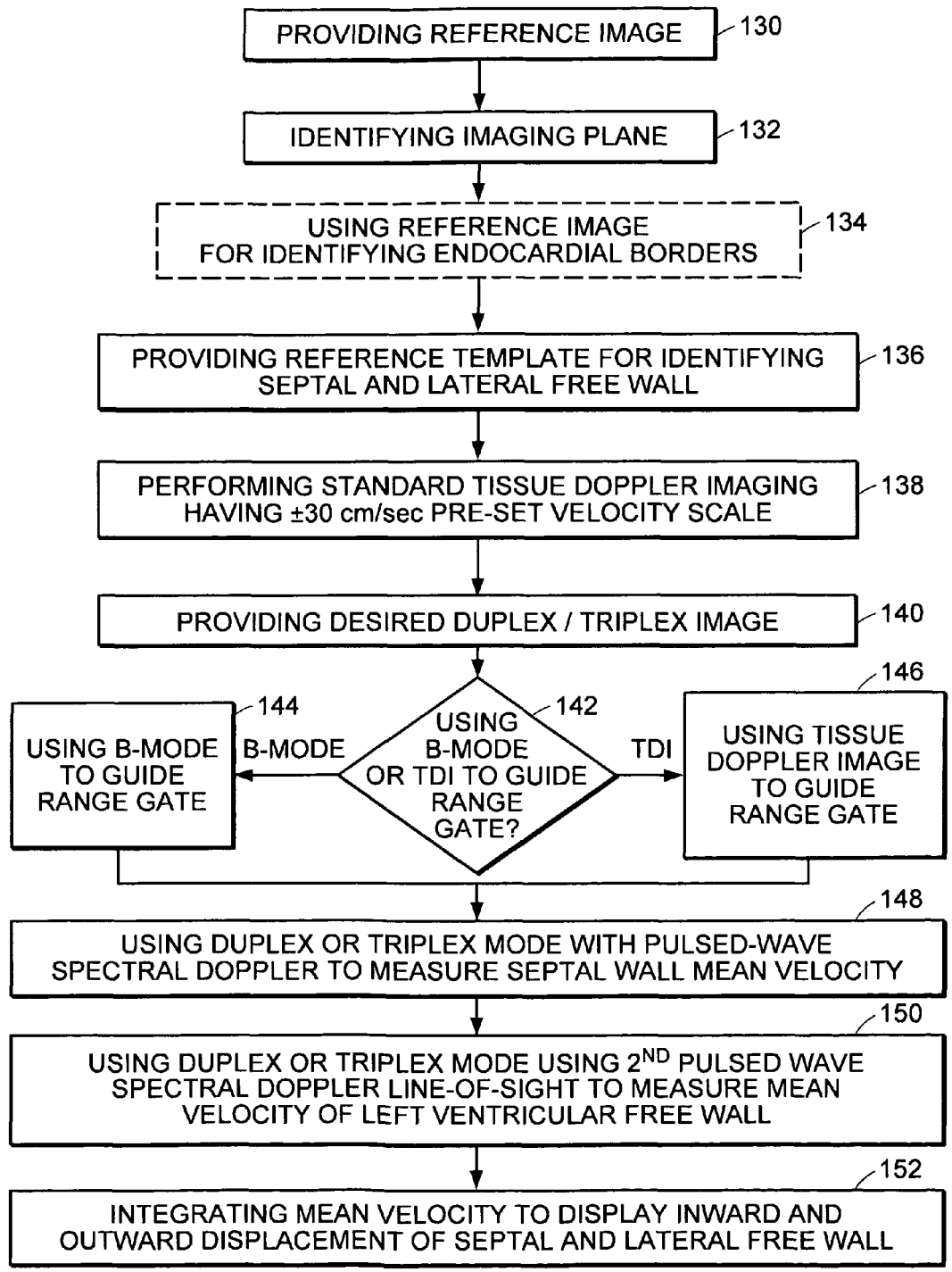
FIG. 7 illustrates an exemplary method for monitoring the synchrony of a heart in accordance with aspects of the invention.
Figure 8:
FIG. 8 illustrates an exemplary display containing an imaging plane capable of showing the four chambers of a heart.

FIG. 7 illustrates an exemplary method for monitoring the synchrony of a heart in accordance with the invention. In the method, a reference template is loaded into memory and used to guide a user in identifying an imaging plane (per step 130). Next a user identifies a desired imaging plane (per step 132). Typically an apical 4-chamber view of the heart is used; however, other views may be used without departing from the spirit of the invention. By way of example, FIG. 8 illustrates an exemplary imaging plane showing the four chambers of a heart.

At times, identification of endocardial borders may be difficult, and when such difficulties are encountered tissue Doppler imaging of the same view may be employed (per step 134). A reference template for identifying the septal and lateral free wall is provided (per step 136). Next, standard tissue Doppler imaging (TDI) with pre-set velocity scales of, say, ±30 cm/sec may be used (per step 138).

Figure 9:
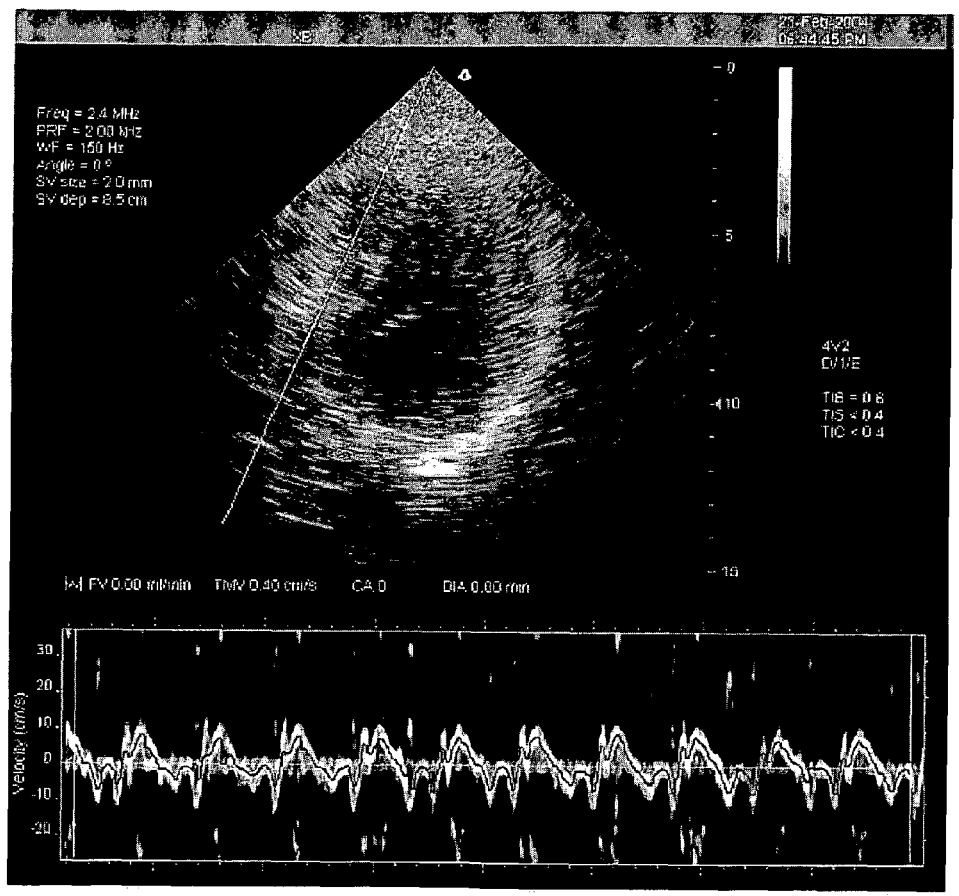
FIG. 9 illustrates an exemplary display employing duplex pulsed wave Tissue Doppler image for facilitating the guiding of range gates and in particular showing a pulsed wave tissue Doppler image.
Figure 10:
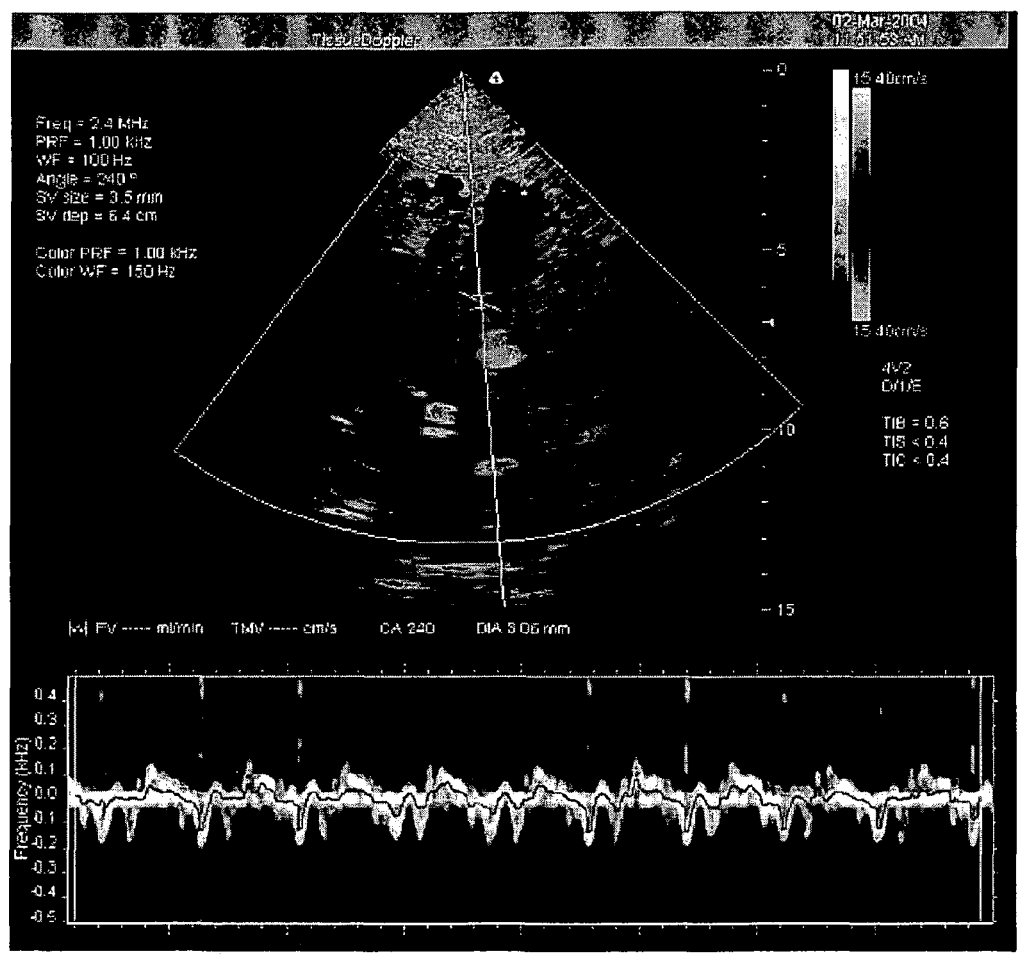
FIG. 10 illustrates an exemplary display employing Triplex tissue Doppler imaging for facilitating the guiding of range gates.

Then, a reference of the desired triplex image may be provided (per step 140). Either B-mode or TDI may be used to guide the range gate (per step 142). FIG. 9 illustrates an exemplary display using B-mode for guiding the range gate (per step 144). In contrast, FIG. 10 illustrates an exemplary display using TDI for guiding the range gate (per step 146). Using TDI or B-mode for guiding the range gate also allows the use of a direction correction angle for allowing the Spectral Doppler to display the radial mean velocity of the septal wall. A first pulsed-wave spectral Doppler is then used to measure the septal wall mean velocity using duplex or triplex mode (per step 148).

Figure 11A:
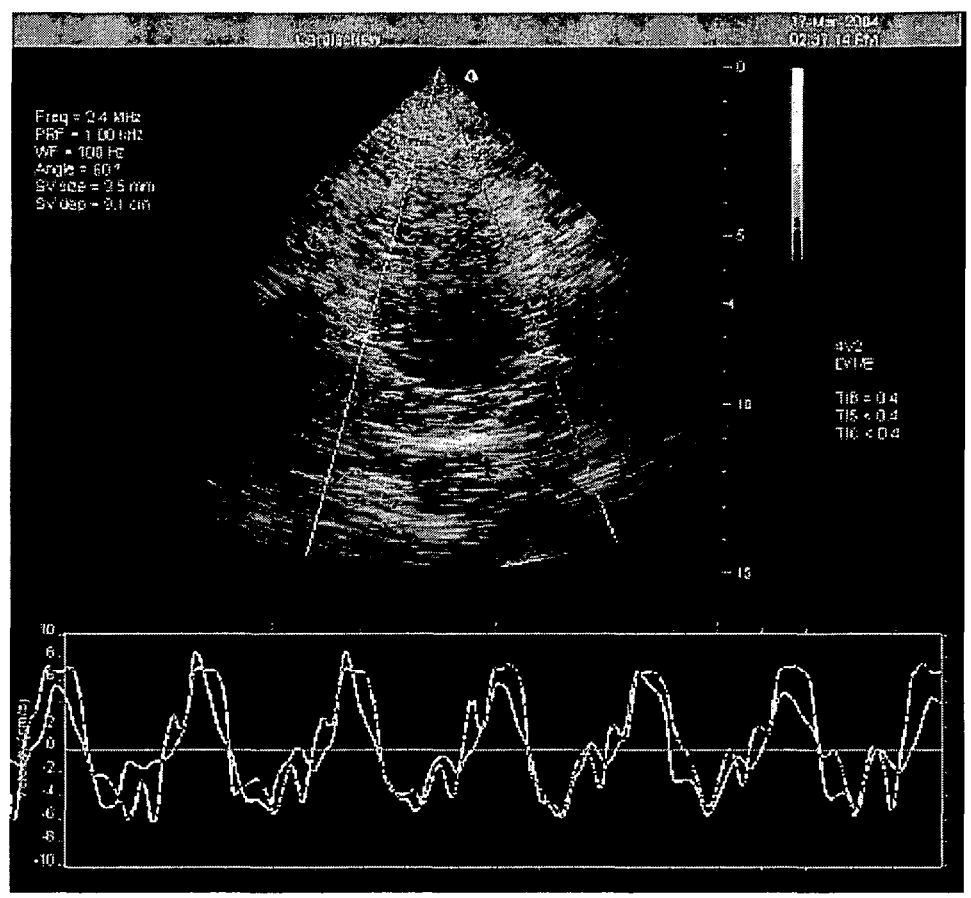
FIG. 11A illustrates an exemplary display containing a duplex image with two spectral lines one each on septal and lateral free walls, respectively, along with a graph illustrating mean velocity.
Figure 11B:
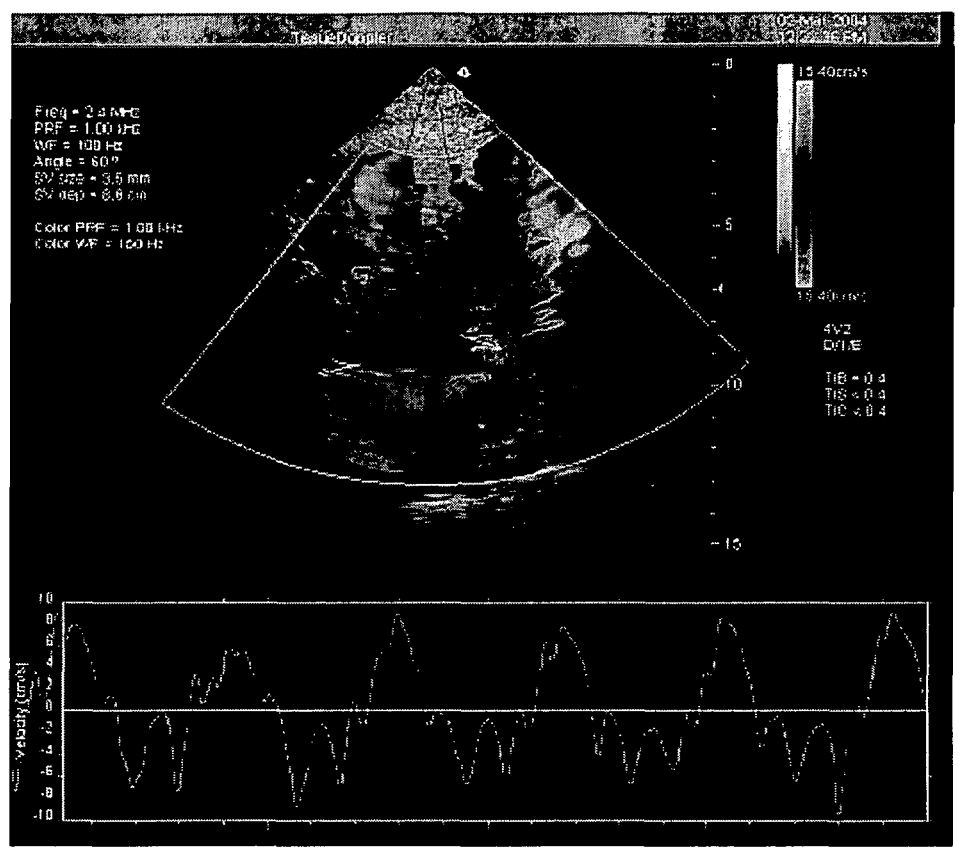
FIG. 11B illustrates an exemplary display containing a triplex image with two spectral lines one each on septal and lateral free walls, respectively, along with a graph illustrating mean velocity.

A second range-gate position is also guided using a duplex image or a TDI (per step 150), and a directional correction angle may be used if desired. Exemplary reference standard duplex, or triplex, images are illustrated in FIGS. 11A and 11B. After step 150, the mean velocity of the septal wall and lateral free wall are being tracked by the system. Time integration of the Spectral Doppler mean velocities at regions of interest (e.g., the septum wall and the left ventricular free wall) then provides the displacement of the septal and left free wall, respectively.

Figure 12:
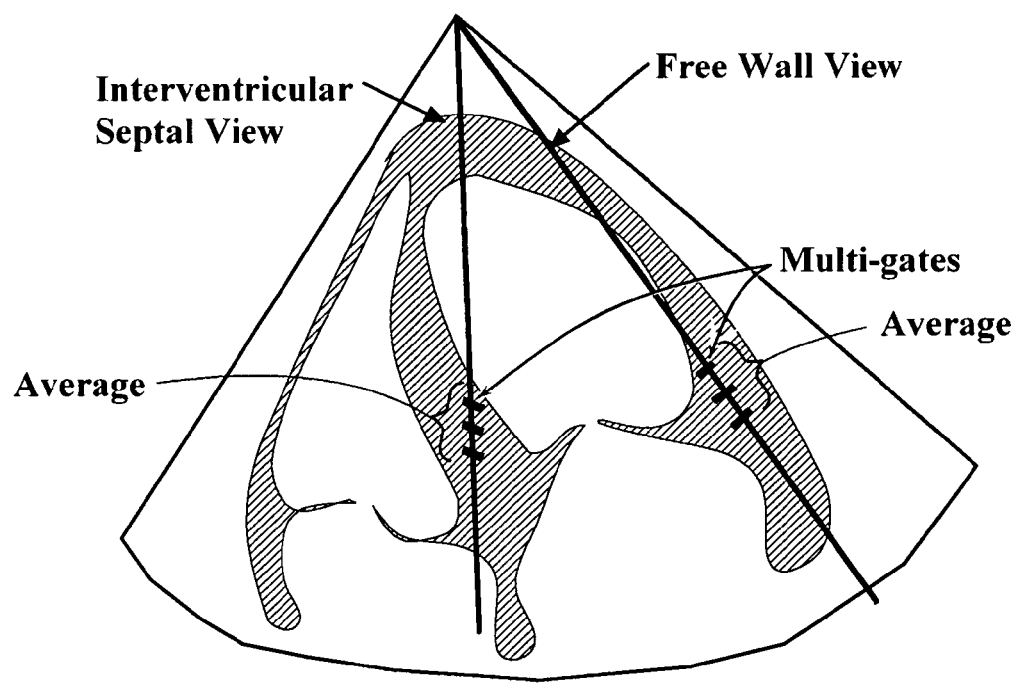
FIG. 12 illustrates an exemplary display showing multi-gate averaging for use with apical four-chamber duplex or triplex tissue Doppler imaging and further useful for achieving at least two PW spectral Doppler views in conjunction with a multi-gate structure along each PW spectral view.
Figure 13A:
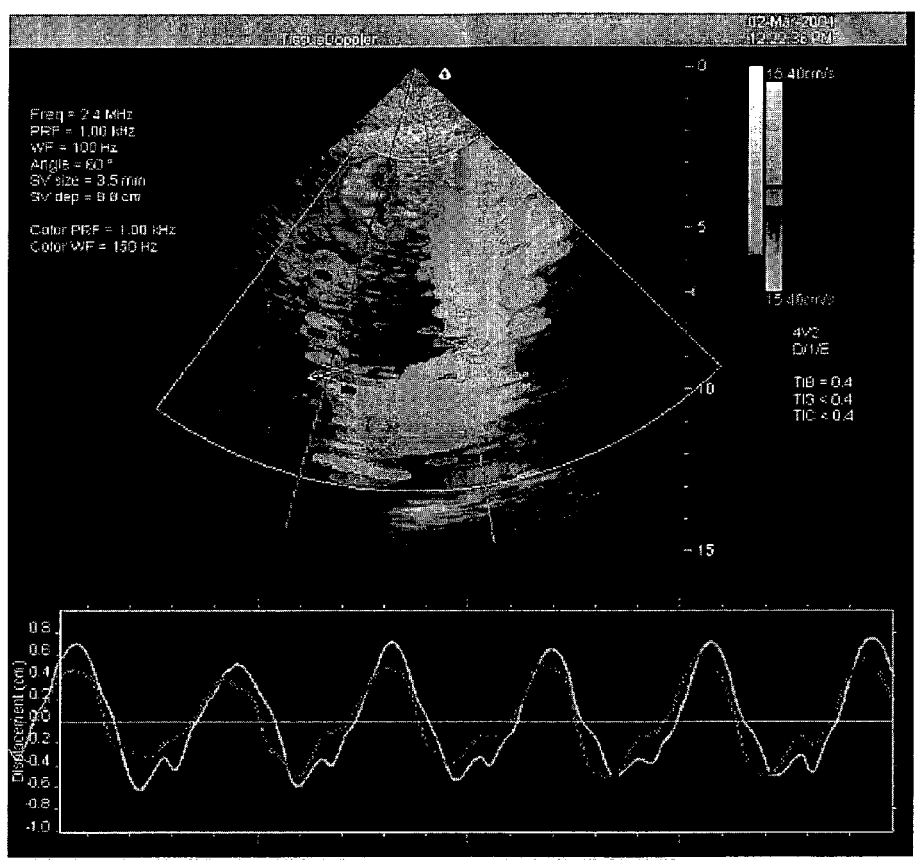
FIG. 13A illustrates an exemplary display having template images depicting normal displacement of left ventricular contractions using triplex with two spectral lines one each on septal and lateral free walls displayed in conjunction with graphs showing displacement.
Figure 13B:
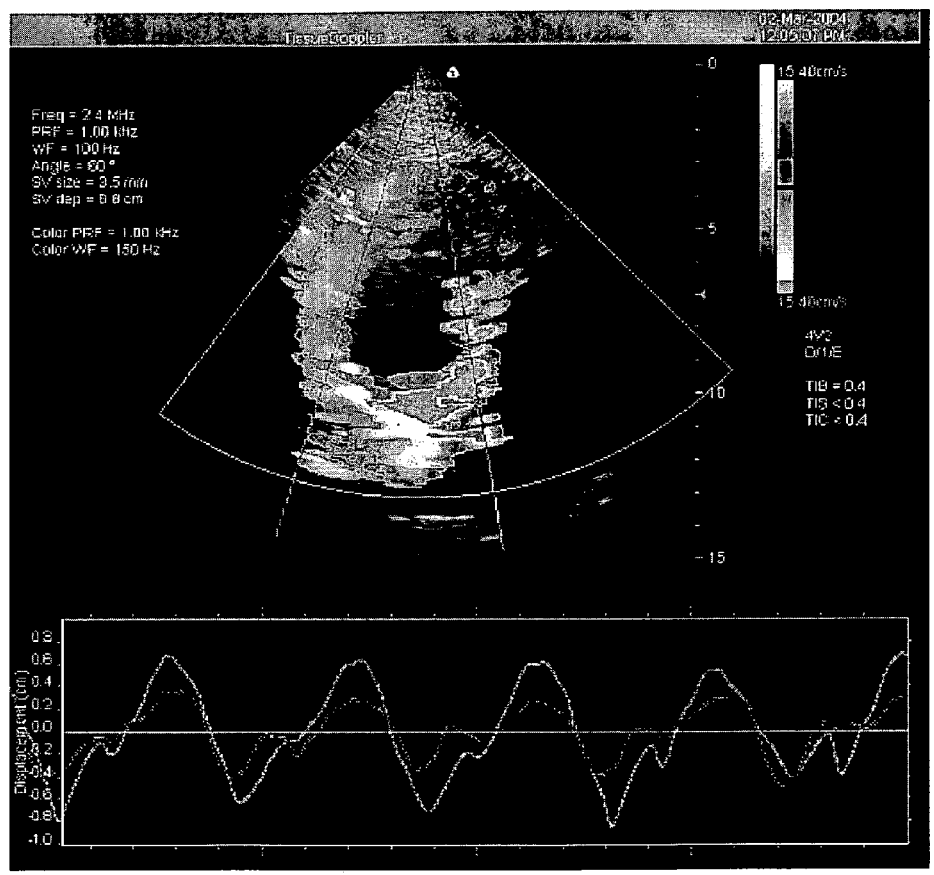
FIG. 13B illustrates an exemplary display having template images depicting dysynchronous left ventricular contraction using triplex with two spectral lines displayed in conjunction with graphs showing displacement.

The above method steps may be utilized in conjunction with a high pass filtering means, analog or digital, known in the relevant arts for removing any baseline disturbance present in collected signals. In addition, the disclosed method, employs multiple simultaneous PW Spectral Doppler lines for tracking movement of the interventricular septum and the left ventricular free wall. In addition, a multiple gate structure may be employed along each spectral line, thus allowing quantitative measurement of regional wall motion. Averaging over multiple gates may allow measurement of global wall movement, an example of which is illustrated in the exemplary display of FIG. 12. The inward and outward displacement of the septal and lateral free wall is then displayed by way of integrating the mean velocity (per step 152). FIGS. 13A and 13B illustrate exemplary template images depicting normal displacement and dysynchronous left ventricular contraction, respectively.

Figure 14:
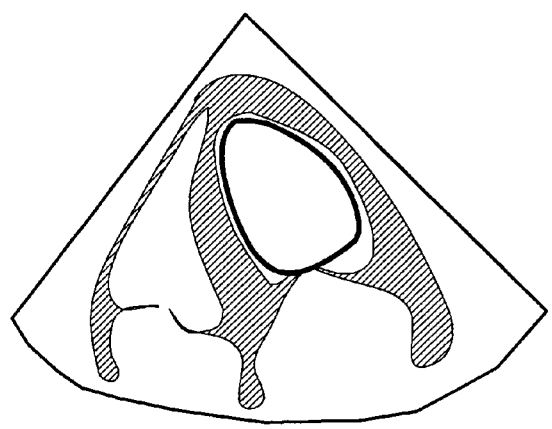
FIG. 14 illustrates an exemplary method of tracking endocardial wall motion using automatic border detection in accordance with aspects of the invention.
Figure 15:
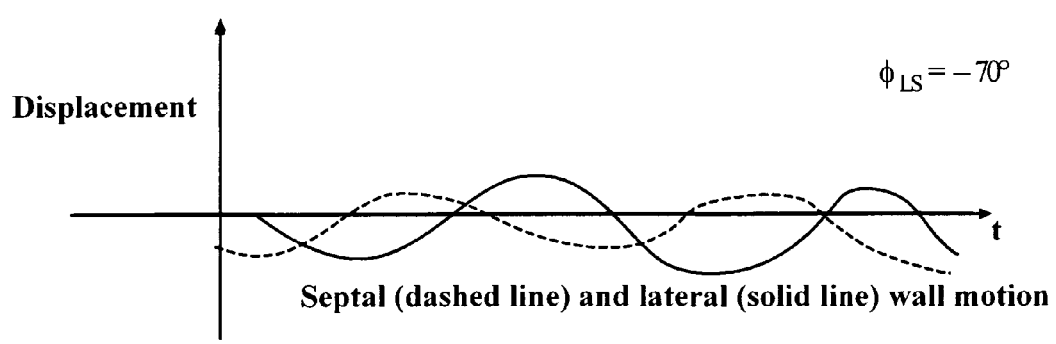
FIG. 15 illustrates an exemplary display showing the derivation of displacements of the septal wall and left ventricular free wall.

Echo phase analysis of radial endocardial wall motion indicates that CRT restores left ventricle synchrony and improves left ventricular functioning. Real-time automatic detection and tracing of ventricular borders is possible using embodiments of the invention and facilitates accurate real-time analysis. FIG. 14 illustrates an exemplary method of tracking endocardial wall motion through the use of automatic border tracking. Tracking wall motion using the method of FIG. 14 is useful when performing phase analysis of wall motion, and FIG. 15 illustrates an exemplary display showing how displacements of the septal wall and left ventricular free wall can be derived using the method of FIG. 14.

Figure 16:
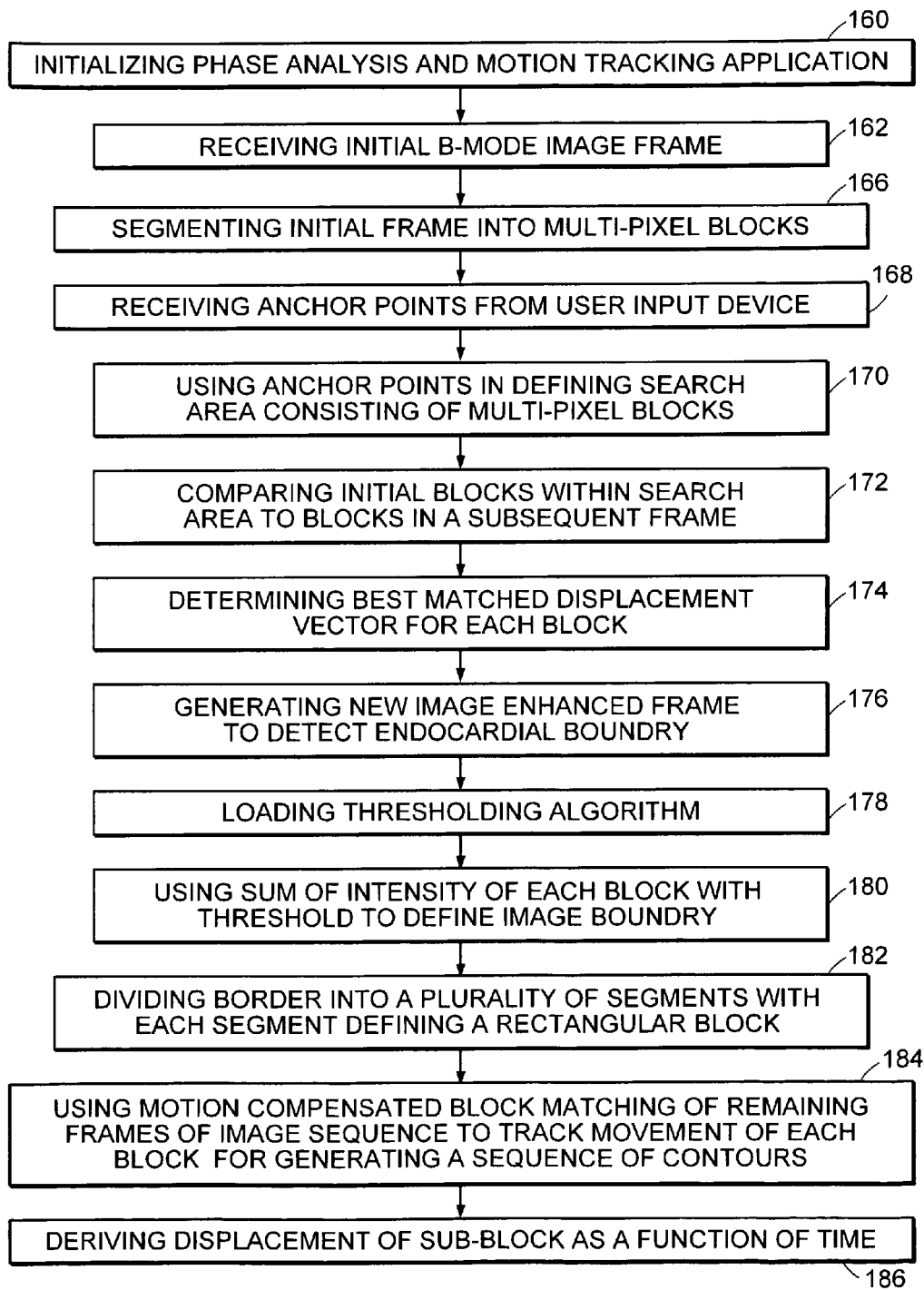
FIG. 16 illustrates an exemplary method for detecting a heart boundary using image data sequences and a motion-compensated block match image enhancement technique.

FIG. 16 illustrates an exemplary method based on B-mode image data sequences and a motion-compensated block-match image enhancement technique to detect the boundary. A B-mode cine loop is an ordered collection of still frames that display sequential "snapshots" of the beating heart as viewed from a particular imaging plane. Thus within a given cine loop, most of the variation in intensity from one frame to the next is due to object motion. Motion-Compensated (MC) image processing refers to mathematical analysis of a sequence of images to account for translation (and possible rotation and deformation) of objects within the field of view.

Figure 17:
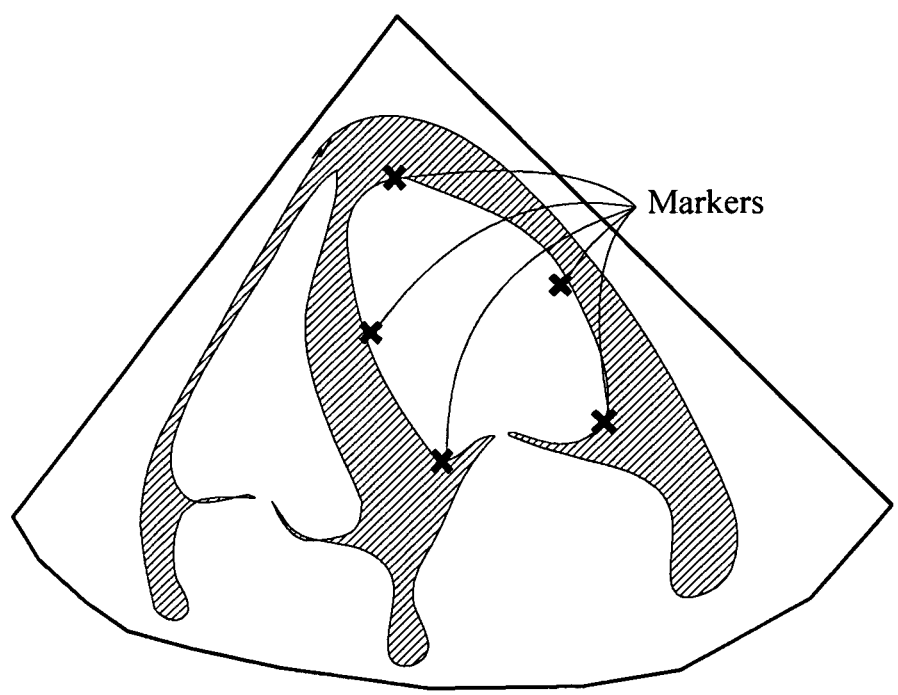
FIG. 17 illustrates an exemplary display containing user defined anchor points consisting of 5 manually placed anchor points on a 4-chamber apical view B-mode image.

The method of FIG. 16 begins by initializing the phase analyses and motion tracking application (per step 160). An initial B-mode image frame is received (per step 162). The image frame is then segmented into multi-pixel blocks (per step 166). A user then marks a set of anchor points on a displayed image using an input device such as a computer mouse, stylus, or keyboard (per step 168). To minimize the computation requirement by reducing the search area, a user is asked to manually place a plurality of, for example 5, "anchor points" along the endocardial border of left ventricle, FIG. 17.

Accurate placement of anchor points by the user is not necessary, since the anchor points are used to derive an approximate boundary. The user-defined anchor points are then used for identifying a search area within the displayed image (per step 170). The search area selected in step 170 is comprised of multi-pixel blocks.

Figure 18:
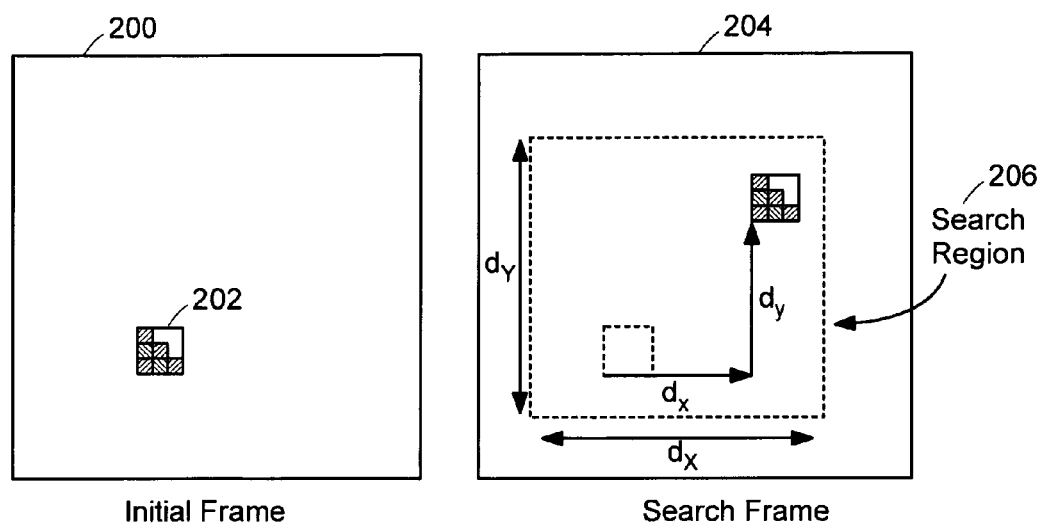
FIG. 18 illustrates a method for using motion compensated block matching to track movement of a block containing image data using a search region defined as $-dx/2 \le x \le dx/2 \ -dy/2 \le y \le dy/2$ and a motion estimated displacement vector of (dx, dy)

The method then compares the initial blocks contained within the search area to image blocks contained in a subsequent image frame (per step 172). A best matched displacement vector is then determined for each block (per step 174). An image-enhanced frame is then generated to detect the endocardial boundary (per step 176). A thresholding algorithm is loaded into the application (per step 178), and the sum of intensity of each block is used with the threshold from step 178 to define an image boundary (per step 180). The border defined by the image boundary is divided into a plurality of segments with each segment defining a rectangular block within the image (per step 182). Motion-compensated block matching of the remaining frames of the image sequence is used to track movement of each block for generating a sequence of contours (per step 184). FIG. 18 illustrates the use of motion-compensated block matching as utilized with aspects of the invention. A current video frame 200, within a sequence of frames, is segmented into small multi-pixel blocks 202. Each block is then compared to blocks in a next frame, here search frame 204, within a pre-defined search area 206 in order to detect the motion of objects.

Matching criteria may be used to extract a displacement vector for a block under analysis. Examples of matching criteria that can be used with the invention are, but are not limited to, the mean absolute difference (MAD), sum of absolute difference as shown in equation 3, $$SAD(d_x, d_y) = \sum_{blcok} |S(x, y) - S(x + d_x, y + d_y)|, \quad (3)$$

or the mean squared difference, sum of square error as shown in equation 4.

$$SSE(d_x, d_y) = \sum_{blcok} [S(x, y) - S(x + d_x, y + d_y)]^2, \quad (4)$$

Figure 19:
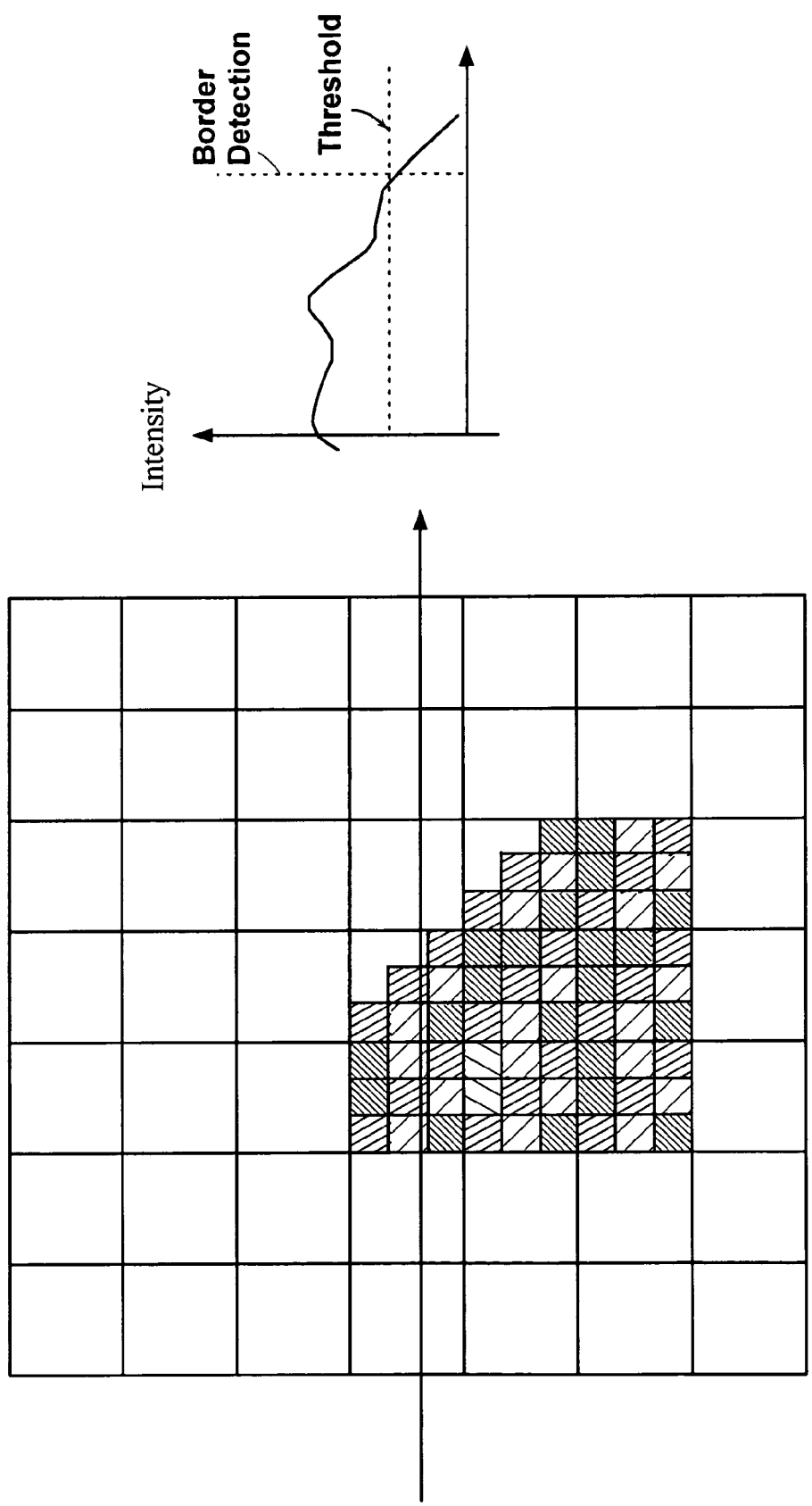
FIG. 19 illustrates an exemplary image block used for border detection in accordance with aspects of the invention.

Both SAD and SSE in general work equally well for estimation of a displacement vector in accordance with aspects of the invention. Once the best-matched displacement vector is detected for each block, a new image-enhanced frame is then formed by a frame average of the motion-compensated initial frame and the second frame. And, this new image-enhanced frame can be used to detect the endocardial boundary. Using the sum of the intensity of each block as a running parameter, a thresholding detection algorithm is used to define the image boundary as shown in FIG. 19. Once the system has defined this initial contour, one can divide the border as a number of segments, where each segment defines a rectangular block. Then a motion-compensated block matching of the remaining frames of the whole image sequence can be used to track the movement of each block, thus generating a sequence of contours. Consequently, a displacement of a sub-block can be derived as a function of time (per step 186).

A motion-compensated block-matching algorithm (BMA) effectively scans a block of pixels in one frame over a larger search area of a next frame and identifies the particular location of the block that provides the highest spatial correlation or best match. Typically, the search area will be specified such that it is likely to contain the maximum anticipated between-frame translation of the original block.

Figure 20:
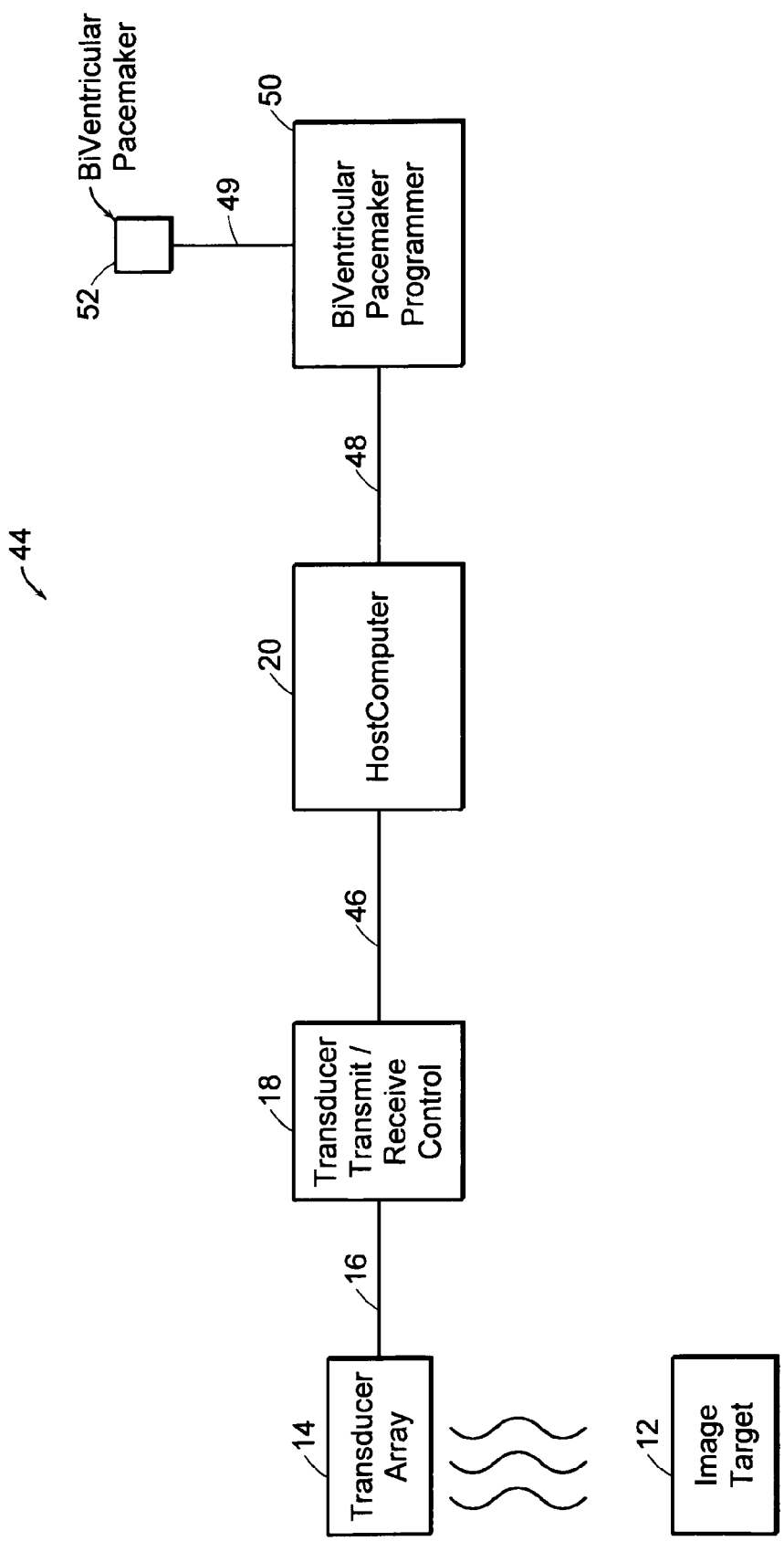
FIG. 20 illustrates an exemplary embodiment of the invention capable of programming a pacemaker in accordance with aspects of the invention.

Embodiments of the invention may be used in conjunction with other medical systems to provide greater utility. For example, an alternative embodiment of the imaging system of FIGS. 1A-C may include apparatus and/or methods for programming pacemakers used to treat patients suffering from heart failure. FIG. 20 contains a system 44 for programming a biventricular pacemaker 52 in real-time. System 44 comprises an image target such as the heart, a transducer array 14, cables 16, a transducer controller 18, an interface 46, and a host computer 20 as shown and previously described in connection with FIGS. 1A-C. In addition, system 44 comprises a programming interface 48, connection 49, a biventricular pacemaker programmer 50, a programming link 48 and a biventricular pacemaker 52.

Programming interface 48 may consist of a hardwired or wireless connection to pacemaker programmer 50. Programming interface 48 may carry raw data received from transducer array 14 or it may convey processed data. Processed data may contain waveforms, parameters, coefficients, or programming instructions. Pacemaker programmer 50 may include general-purpose processing components such as a microprocessor, a bus, a memory, a display and a user input device for processing user input commands, for processing data received over programming interface 48, and for generating programming instructions for outputting to biventricular pacemaker 52.

Pacemaker programmer 50 may be located proximate to a patient and wall motion analyzing system, such as, for example, in an operating room or an examination room. Or, alternatively pacemaker programmer 50 may be located remotely with respect to a wall motion analyzing system and be connected thereto by way of a network, wireless connection, wired connection, or the like.

Connection 49 may include a hardwired connection such as co-axial cable, fiber optic cable, twisted pair cable, etc. or connection 49 may include a wireless connection such as free-space optical, radio-frequency, or acoustic signal. Connection 49 may also include mateable connectors for plugging biventricular pacemaker 52 directly into pacemaker programmer 50. Biventricular pacemaker 52 may comprise a pacemaker capable of operating with a plurality of leads. For example, an embodiment of biventricular pacemaker 52 may include three leads. Two leads may be like those used in conventional dual chamber pacing for placement on the right atrium and right ventricle, respectively, and the third lead may be for placement on the left ventricle for performing biventricular pacing. Biventricular pacemaker 52 may also comprise a microprocessor, a memory, a communications interface and a power source such as a battery. The microprocessor and memory operate cooperatively allowing biventricular pacemaker 52 to monitor heart functions, process data associated therewith, generate optimal stimulation parameters, and apply electrical stimulation as needed to achieve a desired beating sequence for the patient's heart.

Another alternative embodiment of the invention may comprise a wearable ultrasound imaging system that can include a belt mounted computer or interface connected by a cable to hand-held probe. A second hand-held unit may include various controls including a mouse control and buttons to freeze a second hand held displayed image or to store a particular image in electronic memory. The unit can be connected by wireless (RF or infrared) connection or by a hardwire connection to the computer. The computer may further be connected to a desktop, laptop or hand-held display or can be connected by cable to a headmounted, heads-up display system that includes a microphone, a pair of speakers for audio and a high resolution display positioned adjacent the user's eye.

Many changes in the details, materials, and arrangement of parts, herein described and illustrated, can be made by those skilled in the art in light of teachings contained hereinabove. Accordingly, it will be understood that the following claims are not to be limited to the embodiments disclosed herein and can include practices other than those specifically described, and are to be interpreted as broadly as allowed under the law.

What is claimed:

1. A quantitative method for measuring ventricular dysynchrony of a heart comprising:
    actuating a portable ultrasound imaging system including a transducer probe and a hand-held processor housing having a display and a control panel;
    forming a B-mode reference image of moving cardiac tissue including a septal wall and a lateral wall of a heart with the portable ultrasound imaging system;
    using the B-mode reference image to form a first plurality of gates defining a first region of interest of the cardiac tissue including the septal wall, the first plurality of gates being associated with a first pulsed wave spectral Doppler line having a first direction, the B-mode reference image further being used to form a second plurality of gates defining a second region of interest of the cardiac tissue including the lateral wall, the second gate being associated with a second pulsed wave spectral Doppler line having a second direction that is different from the first direction, the first pulsed wave spectral Doppler line and the second pulsed wave spectral Doppler line being rendered in a single image frame for measuring a lateral wall and a septal wall of a heart;
    performing Doppler imaging to obtain pulsed wave spectral Doppler data of the first region of interest using an average movement associated with the first plurality of gates to provide motion data for the septal wall and the second region of interest using an average movement associated with the second plurality of gates to provide motion data for the lateral wall; and
    determining ventricular dysynchrony between the septal wall and the lateral wall using the pulsed wave spectral Doppler data.

2. The method of claim 1 further comprising measuring displacement of the septal wall and the lateral wall of the heart as a function of time for at least a cardiac cycle.

3. The method of claim 1 further comprising displaying simultaneously a measured displacement of the septal wall and the lateral wall of a heart as a function of time for at least a cardiac cycle.

4. The method of claim 1 further comprising determining a velocity of tissue movement within the first region of interest.

5. The method of claim 1 further comprising using automatic border detection to measure tissue movement.

6. The method of claim 1 further comprising triggering image capture using an EKG.

7. The method of claim 1 further comprising determining a directional value to indicate a direction of tissue displacement.

8. The method of claim 1 further comprising providing an apical image of a heart.

9. The method of claim 1 further comprising providing a short axis view of a heart.

10. The method of claim 1 further comprising determining a strain rate of tissue within the region of interest.

11. The method of claim 1 further comprising time integrating the pulsed wave spectral Doppler data to determine displacement of tissue within the region of interest.

12. The method of claim 1 further comprising measuring dysynchronous ventricular movement of the left ventricle of the heart.

13. The method of claim 12 further comprising displaying a B-mode image and simultaneously displaying displacement of an interventricular septal wall and a left free wall of a heart as a function of time for at least a cardiac cycle to display dysynchronous ventricular movement of the heart.

14. The method of claim 1 further comprising providing a reference image to guide echocardiographic imaging operations and obtain quantitative data representative of heart wall motion.

15. The method of claim 1 further comprising using a first plurality of gates to measure a velocity of an epicardial region of the septal wall and a second plurality of gates to measure a velocity of an endocardial region of the septal wall.

16. The method of claim 1 further comprising using a plurality of anchor points to define a heart wall boundary.

17. The method of claim 1 further comprising using a pair of spectral Doppler lines to indicate a thickness of the septal wall.

18. The method of claim 1 further comprising using a phase relationship of heart wall displacement to determine dysynchrony.

19. The method of claim 1 further comprising performing high pass filtering of ultrasound data.

20. The method of claim 1 further comprising using tissue Doppler imaging to guide a range gate with a pre-set velocity scale.

21. The method of claim 1 further comprising forming a tissue Doppler image of the tissue, and forming at least one gate using the tissue Doppler image.

22. The method of claim 1 further comprising displaying displacement of the septal wall and the lateral wall during a plurality of cardiac cycles.

23. The method of claim 1 further comprising determining ventrical dysychrony during a single cardiac cycle.

24. The method of claim 1 further comprising connecting the ultrasound system to a pacemaker programmer device.

25. The method of claim 1 wherein the processor housing comprises a data processing device and a memory having stored therein a sequence of instructions for performing measurement of ventricular dysynchrony.

26. The method of claim 25 wherein the processor housing further comprises a beamforming device, a single board computer and a display mounted thereon.

* * * * *